US010465171B2

(12) United States Patent
Liu et al.

(10) Patent No.: US 10,465,171 B2
(45) Date of Patent: Nov. 5, 2019

(54) 7β-HYDROXYSTEROID DEHYDROGENASES AND THEIR USE

(71) Applicant: PharmaZell GmbH, Raubling (DE)

(72) Inventors: Lou Liu, Beijing (CN); Rolf Schmid, Stuttgart (DE); Arno Aigner, Tuntenhausen (DE)

(73) Assignee: PharmaZell GmbH, Raubling (DE)

( * ) Notice: Subject to any disclaimer, the term of this patent is extended or adjusted under 35 U.S.C. 154(b) by 0 days.

(21) Appl. No.: 15/918,757

(22) Filed: Mar. 12, 2018

(65) Prior Publication Data
US 2018/0273916 A1 Sep. 27, 2018

Related U.S. Application Data

(63) Continuation of application No. 15/077,954, filed on Mar. 23, 2016, which is a continuation of application No. 13/512,166, filed as application No. PCT/EP2010/068576 on Nov. 30, 2010.

(30) Foreign Application Priority Data

Nov. 30, 2009 (EP) ..................................... 09177544
Aug. 25, 2010 (EP) ..................................... 10008837

(51) Int. Cl.
C12N 9/04 (2006.01)
C12P 33/00 (2006.01)
C12P 33/02 (2006.01)
C12P 33/06 (2006.01)

(52) U.S. Cl.
CPC ............ *C12N 9/0006* (2013.01); *C12P 33/00* (2013.01); *C12P 33/02* (2013.01); *C12P 33/06* (2013.01); *C12Y 101/01201* (2013.01)

(58) Field of Classification Search
None
See application file for complete search history.

(56) References Cited

U.S. PATENT DOCUMENTS 7,635,572 B2  12/2009  Zhou et al.
9,096,825 B2   8/2015  Schmid et al.

OTHER PUBLICATIONS

Sudarsanam et al. Draft Genome sequence of Collinsella aerofaceins (ATCC 25986) from UniPro submitted 2007 accession No. A4ECA9.
Lehninger, A. "Biochemistry" (1975) (Worth Publishers, line.: Newy York, NY) p. 481.
Witkowski et al. Biochemistry (1999) 38: 11643-11650.
Whisstock et al. Quarterly Reviews of Biophysics (2003) 36(3): 307-340.
P. Sudarsanam et al., Database UniProt [Online] "Putative uncharacterized protein" (Apr. 17, 2007), XP002579158, Database accession No. A4ECA9.

(Continued)

*Primary Examiner* — Richard C Ekstrom
(74) *Attorney, Agent, or Firm* — Saul Ewing Arnstein & Lehr LLP; Peter C. Lauro

(57) ABSTRACT

The invention relates to novel 7β-hydroxysteroid dehydrogenases which are obtainable from bacteria of the genus *Collinsella*, especially of the strain *Collinsella aerofaciens*, to the sequences encoding said enzymes, to methods for producing said enzymes and to their use in the enzymatic conversion of cholic acid compounds, and especially in the production of ursodeoxycholic acid (UDCS). The invention also relates to novel methods for the synthesis UDCS.

22 Claims, 8 Drawing Sheets

Specification includes a Sequence Listing.

(56) References Cited

OTHER PUBLICATIONS

S. Hirano et al., "Characterization of NADP-dependent 7 beta-hydroxysteroid dehydrogenases from 2 Peptostreptococcus products and Eubacterium aerofaciens", Applied and Environmental Microbiology, vol. 43, No. 5, pp. 1057-1063 (May 1982).
T. Akao et al., "Purification and characterization fo 7 beta-hydoxysteriod dehydrogenaqse from *Ruminococcus* sp. of 3 human intestine", Journal of Biochemistry, Japanese Biochemical Society, vol. 102, No. 3, pp. 613-619 (Jan. 1987).
C. Giacomo et al., "Enzymatic synthesis of 12-ketoursodeoxycholic acid from dehydrocholic acid in a membrane reactor", Biotechnology Letters, vol. 14, No. 12, pp. 1131-1134 (1992).
R. Bovara et al., "A new enzymatic route to the synthesis of 12-ketoursodeoxycholic acid", Biotechnology Letters, vol. 18, No. 3, pp. 305-308 (1996).
L. Luo et al., Identification, cloning, heterologous expression, and characterization of a NADPH-dependent 7[beta]-6 hydroxysteroid dehydrogenase from Collinsella aerofaciens, Applied Microbiology and Biotechnology, vol. 90, No. 1, pp. 127-135 (Apr. 2011).
Hirano et al. App. Environ. Microbiol. (1982) 43(5): 1057-1063.
Database Sheet for ATCC 29986 downloaded from www.ATCC.org on Sep. 6, 2014.
Carrera et al. Biotechnol. Lett. (1992) 14(12): 1131-1135.
Form PCT/ISA/210—ISR for PCT/EP2010/068576 (dated May 9, 2011).
Form PCT/IB/373—Written Opinion for PCT/EP2010/068576 (dated May 2012).

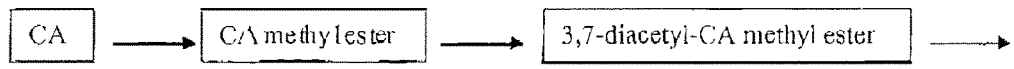
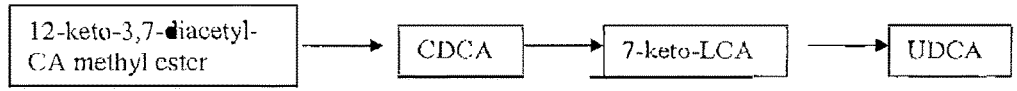
Fig. 1a
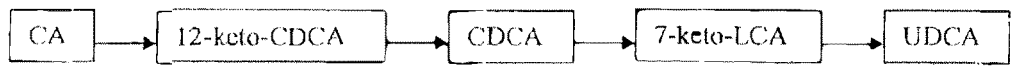
Fig. 1b
Fig. 1c
Fig. 1d
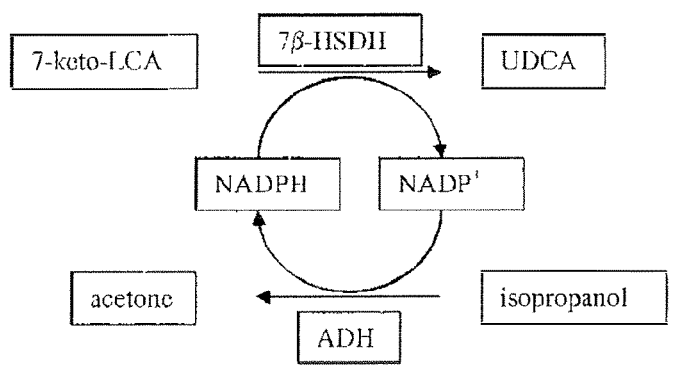
Fig. 1e Accession: ZP_01773061

```
  1 mnlrekygew glilgategv gkafcekiaa ggmnvvmvgr reeklnvlag eiretygvet
 61 kvvradfsqp gaaetvfaat egldmgfmsy vaclhsfgki qdtpwekhea minvnvvtfl
121 kcfhhymrif aaqdrgavin vssmtgisss pwngqygagk afilkmteav acecegtgvd
181 vevitlgttl tpsllsnlpg gpqgeavmki altpeecvde afeklgkels viagqrnkds
241 vhdwkanhte deyirymgsf yrd
```

Fig. 2a

Accession No.: NZ_AAVN02000010, Region: 52005..52796

```
  1 atgaacctga gggagaagta cggtgagtgg ggcctgatcc tgggcgcgac cgagggcgtc
 61 ggcaaggcgt tctgcgagaa gatcgccgcc ggcggcatga acgtcgtcat ggtcggccgt
121 cgcgaggaga agctgaacgt gctcgcaggc gagatccgcg agacctacgg cgtggagacc
181 aaggtcgtgc gcgccgactt tagccagccc ggcgctgccg agaccgtctt cgccgcgacc
241 gagggcctgg acatgggctt catgagctac gtggcctgcc tgcacagctt cggtaagatc
301 caggacaccc cctgggagaa gcacgaggcc atgatcaacg tcaacgtcgt gaccttcctc
361 aagtgcttcc accactacat gcggatcttt gccgcccagg accgcggcgc cgtgatcaac
421 gtctcgtcga tgaccggcat cagctccagc ccctggaacg gccagtacgg cgcgggcaag
481 gccttcatcc tcaagatgac cgaggccgtg cctgcgagt gcgagggcac cggcgtcgac
541 gtcgaggtca tcaccctcgg caccacccta accccagcc tgctgtccaa cctccccggc
601 ggcccgcagg gcgaggccgt catgaagatc gccctcaccc ccgaggagtg cgttgacgag
661 gcctttgaga agctgggtaa ggagctctcc gtcatcgccg gccagcgcaa caaggactcc
721 gtccacgact ggaaggcaaa ccacaccgag gacgagtaca tccgctacat ggggtcgttc
781 taccgcgact ag
```

Fig. 2b

3alpha-HSDH

Source: *Comamonas testosteroni* ATCC 11996

```
  1 msiivisgca tgigaatrkv leaaghqivg idirdaevia dlstaegrkq aiadvlakcs
 61 kgmdglvlca glgpqtkvlg nvvsvnyfga telmdaflpa lkkghqpaav vissvasahl
121 afdknplala leageeakar aivehageqg gnlayagskn altvavrkra aawgeagvrl
181 ntiapgatet pllqaglqdp rygesiakfv ppmgrraeps emasviaflm spaasyvhga
241 qividggida vmrptqf
```

Fig. 2c

Nucleic acid sequence coding for 3alpha-HSDH

Source: *Comamonas testosteroni* ATCC 11996

Accession: AF092031, Region: 158..931

```
  1 atgtccatca tcgtgataag cggctgcgcc accggcattg gtgcggctac gcgcaaggtc
 61 ctggaggcgg ccggtcacca gatcgtaggc atcgatatac gcgatgcgga agtgattgcc
121 gatctctcga cggccgaagg tcgaaagcag gcgattgccg atgtactggc gaagtgcagc
181 aagggcatgg acggcctggt gctgtgcgcc ggcctgggac cgcagaccaa ggtgcttggc
241 aatgtggttt cggtcaatta ttttggcgcg accgagctga tggatgcctt tttgccagcg
301 ctgaaaaaag gccatcagcc cgcagccgtc gtcatctcgt ccgtggcttc cgcgcatctg
361 gcttttgaca gaacccact ggcgctggca ctggaagccg gcgaggaagc caaggcccgc
421 gccattgtcg aacatgcggg agagcagggc ggaaatctgg cctatgcggg cagcaagaat
481 gctttgacg tggctgtgcg caaacgcgcc gccgctggg gcgaggctgg cgtgcgcctg
541 aacaccatcg ccccggtgc aaccgagact cccttgctgc aggcgggcct gcaggacccg
601 cgctatggcg aatccattgc caagttcgtt cctcccatgg gccgccgtgc cgagccgtcc
661 gagatggcgt cggtcatcgc cttttttgatg agcccggccg caagctatgt gcatggcgcg
721 cagatcgtca ttgatggcgg cattgatgcg gtgatgcgcc cgacacagtt ctga
```

Fig. 2d

3alpha-HSDH

Source: Rattus norvegicus (Norway rat)
Genbank ACCESSION M61937

MDSISLRVALNDGNFIPVLGFGTTVPEKVAKDEVIKATKIAIDN
GFRHFDSAYLYEVEEEVGQAIRSKIEDGTVKREDIFYTSKLWSTFHRPELVRTCLEKT
LKSTQLDYVDLYIIHFPMALQPGDIFFPRDEHGKLLFETVDICDTWEAMEKCKDAGLA
KSIGVSNFNCRQLERILNKPGLKYKPVCNQVECHLYLNQSKMLDYCKSKDIILVSYCT
LGSSRDKTWVDQKSPVLLDDPVLCAIAKKYKQTPALVALRYQLQRGVVPLIRSFNAKR
IKELTQVFEFQLASEDMKALDGLNRNFRYNNAKYFDDHPNHPFTDE

Fig. 2e

```
atggattcca tatctctgcg tgtagcacta aatgatggta acttcattcc tgtactgggg
tttggaacca ctgtgcctga gaaggttgct aaggatgaag ttatcaaggc tactaaaata
gctatagata atggattccg ccattttgac tctgcttatt tgtacgaagt agaagaggaa
gtgggccaag ccattagaag caagattgaa gacggactg tgaagagaga agatatattc
tatacttcaa agctttggag cactttccat agaccagagc tggtccgaac ttgcttggaa
aagacactga aaagcactca actggactat gtggatcttt atattattca tttcccaatg
gctttgcagc ctgagatat ttttttccca cgagatgagc atggaaaact attgtttgaa
acagtggata tctgtgacac atgggaggcc atggaaaagt gtaaggatgc aggattggcc
aagtctattg gggtgtccaa ctttaactgc aggcagctgg agaggattct gaataagcca
gggctcaaat acaagcctgt gtgcaaccag gtggaatgtc acctttatct caaccagagc
aaaatgctgg actattgtaa gtcaaaagac atcattctgg tttcctactg cacgctggga
agttcacgag acaaaacatg ggtggatcag aaaagtccag ttctcctaga tgatccagtt
ctttgtgcca tagcaaagaa gtacaagcaa accccagccc tagttgccct tcgctaccag
ctgcagcgtg gggttgtgcc cctgatcagg agtttcaacg cgaagcggat caaagagcta
acacaggttt ttgaattcca gttggcttca gaggacatga aagccctgga tggcttgaac
agaaatttca gatacaacaa tgcaaaatat tttgatgacc atcccaatca tccatttact
gatgaatag
```

7β-HYDROXYSTEROID DEHYDROGENASES AND THEIR USE

RELATED APPLICATION DATA

This application is a continuation of U.S. application Ser. No. 15/077,954, filed Mar. 23, 2016, pending, which is a continuation of U.S. application Ser. No. 13/512,166, filed Oct. 23, 2012, which is the U.S. national phase, pursuant to 35 U.S.C. § 371, of PCT international application Ser. No. PCT/EP2010/068576, filed Nov. 30, 2010, designating the United States and published in German on Jun. 3, 2011 as publication WO 2011/064404 A1, which claims priority to European Application Serial Nos. EP 09177544.5, filed Nov. 30, 2009, and EP 10008837.6, filed Aug. 25, 2010. The entire contents of the aforementioned patent applications are incorporated herein by this reference.

The invention relates to novel 7β-hydroxysteroid dehydrogenases obtainable from bacteria of the genus *Collinsella*, in particular of the strain *Collinsella aerofaciens*, the sequences coding for these enzymes, methods for the production of the enzymes and the use thereof in enzymatic conversions of cholic acid compounds, and in particular in the production of ursodesoxycholic acid (UDCA); also a subject of the invention are novel methods for the synthesis of UDCA,

BACKGROUND OF THE INVENTION

The active substances ursodesoxycholic acid (UDCA) and the corresponding diastereomer chenodesoxycholic acid (CDCA) have for many years been used for the medicinal treatment of gallstone problems. The two compounds differ only in the configuration of the hydroxy group on C atom 7 (UDCA: (3 configuration, CDCA: a configuration). For the production of UDCA, various methods are described in the state of the art, which are carried out purely chemically or consist of a combination of chemical and enzymatic process steps. In each case the starting point is cholic acid (CA) or CDCA produced from cholic acid.

The classical chemical method for UDCA production is shown schematically in FIG. 1a. A serious disadvantage of the classical method inter alia is as follows: because the chemical oxidation is not selective, the carboxy group and the 3α and 7α-hydroxy group must be protected by esterification.

An alternative chemical/enzymatic method based on the use of the enzyme 12α-hydroxy-steroid dehydrogenase (12α-HSDH) is shown schematically in FIG. 1b and is, for example, described in PCT/EP2009/002190 from the present applicant. In this alternative method, the 12α-HSDH selectively oxidizes CA to 12-keto-CDCA. The two protection steps necessary according to the classical chemical method are thereby rendered superfluous.

Further, Monti, D., et al., (*One-Pot Multienzymatic Synthesis of 12-Ketoursodeoxycholic Acid: Subtle Cofactor Specificities Rule the Reaction Equilibria of Five Biocatalysts Working in a Row*. Advanced Synthesis & Catalysis, 2009) describe an alternative enzymatic-chemical method that is shown schematically in FIG. 1c. In this alternative, the CA is first oxidized by 7α-HSDH from *Bacteroides fragilis* ATCC 25285 (Zhu, D., et al., *Enzymatic enantioselective reduction of α-ketoesters by a thermostable 7α-hydroxysteroid dehydrogenase from Bacteroides fragilis*. Tetrahedron, 2006. 62(18): p. 4535-4539) and 12α-HSDH to 7,12-diketo-LCA. These two enzymes are each NADH-dependent. After the reduction by 7β-HSDH (NADPH-dependent) from *Clostridium absonum* ATCC 27555 (DSM 599) (MacDonald, I. A. and P. D. Roach, *Bile induction of 7 alpha-and 7 beta-hydroxysteroid dehydrogenases in Clostridium absonum*. Biochim Biophys Acta, 1981. 665(2): p. 262-9), 12-keto-UDCA is formed. The final product is obtained by Wolff-Kishner reduction. Disadvantages in this method are that because of the equilibrium position of the catalyzed reaction a complete conversion is not possible, and that for the first step of the conversion two different enzymes must be used, which increases the process cost. For cofactor regeneration, lactate dehydrogenase (LDH; for regeneration of NAD$^+$) and glucose dehydrogenase (GlcDH, for regeneration of NADPH) are used. A disadvantage in the cofactor regeneration used there is that the coproduct formed can only be removed from the reaction mixture with great difficulty, so that the reaction equilibrium cannot be favorably influenced, which results in incomplete conversion of the educt.

A 7β-HSDH from the strain *Collinsella aerofaciens* ATCC 25986 (DSM 3979; formerly *Eubacterium aerofaciens*) was described in 1982 by Hirano and Masuda (Hirano, S. and N. Masuda, *Characterization of NADP-dependent 7 beta-hydroxysteroid dehydrogenases from Peptostreptococcus productus and Eubacterium aerofaciens*. Appl Environ Microbiol, 1982. 43(5): p. 1057-63). Sequence information on this enzyme was not disclosed. The molecular weight determined by gel filtration was 45,000 Da (see Hirano, page 1059, left-hand column). Further, for the enzyme there, the reduction of the 7-oxo group to the 7β-hydroxy group could not be observed (see Hirano, page 1061, discussion 1st paragraph). Similarly, Hirano et al also disclosed $K_M$ and $V_{max}$ values only for NADP$^+$ (0.4 and 0.2 respectively) but not for NADPH. Those skilled in the art thus recognize that the enzyme described by Hirano et al is not suitable for the catalysis of the reduction of DHCA in the 7 position to 3,12-diketo-7β-CA.

Although the genome of *Collinsella aerofaciens* ATCC 25986 was already sequenced in 2007, none of the analyzed sequence motifs therein could be assigned to a potential short-chain dehydrogenase, to which enzyme family the HSDH enzymes belong.

In Biotechnology Letters 1992, 14,12, 1131-1135, Carrea et al describe a method for the production of UDCA from CA with the use of an enriched 7β-HSDH and a 3α-HSDH. However, a disadvantage in this method is the use of a 7β-HSDH from the pathogenic microorganism *Clostridium absonum*, and the need preparatively to purify the enzyme from the bacterial extract which additionally possesses undesired 7α-HSDH activity.

Hence the purpose of the invention is the provision of a novel method for the production of UDCA which avoids the aforesaid disadvantages. In particular, a novel enzyme which catalyzes the stereospecific reduction of DHCA in the 7-position to 3,12-diketo-7β-CA should be provided.

A further purpose consists in the provision of novel 7β-HSDH enzymes which for example are usable in the preparation of UDCA, and in particular catalyze the stereo- and enantioselective oxidation/reduction of cholic acid derivatives in the 7-position.

SUMMARY OF THE INVENTION

Surprisingly, these problems could be solved through the isolation and characterization of a novel regio- and stereo-specific 7β-HSDH from aerobic bacteria of the genus *Collinsella*, in particular of the strain *Collinsella aerofaciens* and the use thereof in the conversion of cholic acid compounds, in particular in the production of UDCA.

According to the invention, a novel method of UDSC production is in particular provided, which is shown schematically in FIG. 1d.

In accordance with the invention, the oxidation of CA is effected simply in a classical manner. The DHCA is reduced to 12-keto-UDCA by 7β-HSDH and 3α-HSDH individually one after the other or in one pot. Combined with the Wolff-Kishner reduction, UDCA can thus be synthesized from CA in just three steps.

Advantages here are inter alia that the enzymatic reaction enables high conversion, displays high selectivity and does not form byproducts. The recombinantly produced enzymes 7β-HSDH and 3α-HSDH surprisingly advantageously enable the large-scale production of UDCA.

BRIEF DESCRIPTION OF THE DRAWINGS

FIG. 1a is a schematic representation of the classical chemical method for UDCA production. FIG. 1b is a schematic representation of an alternative chemical/enzymatic method for UDCA production based on the use of the enzyme 12a-hydroxy-steroid dehydrogenase (12α-HSDH). FIG. 1c is a schematic representation of a further alternative method for UDCA production. FIG. 1d is a schematic representation of the method for UDSC production in accordance with the invention. FIG. 1e is a schematic representation of reaction Scheme 1 for the reduction of 7-keto-LCA by the 7β-HSDH.

FIG. 2a shows the amino acid sequence of the 7β-HSDH from *Collinsella aerofaciens* and FIG. 2b the coding nucleic acid sequence for the amino acid sequence of FIG. 2a; FIG. 2c shows the amino acid sequence of the 3α-HSDH from *Comanomonas testosteroni* and FIG. 2d the coding nucleic acid sequence for the amino acid sequence of FIG. 2c; FIG. 2e shows the amino acid sequence of the 3α-HSDH from *Rattus norvegicus* and FIG. 2f the coding nucleic acid sequence for the amino acid sequence of FIG. 2e.

FIG. 4 shows the sequence alignment of 7β-HSDH from *Collinsella aerofaciens* DSM 3979 and selected HSDH proteins. Conserved residues in the sequences are highlighted in color. The following sequence deposition numbers apply: 116-HSDH from *Homo sapiens*, GenBank NP_005516; 11β-HSDH from *Mus_musculus*, GenBank NP_001038216; 11β-HSDH from *Cavia porcellus*, GenBank AAS47491; 7α-HSDH from *Brucella melitensis*, GenBank NP_698608; 7α HSDH from *Escherichia coli*, GenBank NP_288055; 7α-HSDH from *Clostridium sordellii*, GenBank P50200; 3α/20β-HSDH from *Streptomyces exfoliates*, Swiss-Port P19992; 3β/17β-HSDH from *Comamonas testosteroni* GenBank AAA25742; 3α-HSDH from *Pseudomonas*_sp, GenBank BAA08861; 3α-HSDH from *Comamonas testosteroni*, GenBank YP_003277364; 17β-HSDH from *Homo sapiens*, GenBank NP_000404 and 20β-HSDH from *Sus scrofa*, GenBank NP_999238. The last 17 amino acids of 17β-HSDH from *Homo sapiens* and the last amino acid of 2013-HSDH from *Sus scrofa* are no longer shown in the alignment, since no additional alignment information was derivable therefrom.

Figure 1F:
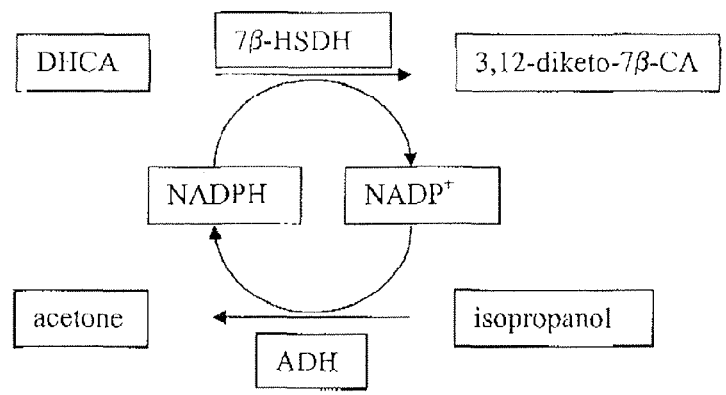
FIG. 1f is a schematic representation of reaction Scheme 2 for the reduction of DHCA by the 7β-HSDH.

SPECIFIC EMBODIMENTS OF THE INVENTION 1. 7β-hydroxysteroid dehydrogenase (7β-HSDH) obtainable from an anaerobic bacterium, in particular of the genus *Collinsella*, such as the strain *Collinsella aerofaciens* DSM 3979 (ATCC 25986) and functional equivalents derived therefrom.

The 7β-HSDH obtainable according to the invention from *Collinsella aerofaciens* DSM 3979 is characterized in particular by at least one more of the following properties, such as for example 2, 3, 4, 5, 6 or 7 or all such properties:

a) Molecular weight (SDS gel electrophoresis): about 28-32 kDa, in particular about 29 to 31 kDa or about 30 kDa;

b) Molecular weight (gel filtration, under non-denaturing conditions, such as in particular without SDS): about 53 to 60 kDa, in particular about 55 to 57 kDa, such as 56.1 kDa, whereby the enzyme according to the invention differs markedly from the 7B-HSDH enzyme from *C. aerofaciens* ATCC25986 with 45 kDa described by Hirano et al (see above). This confirms the dimeric nature (quartet structure) of the 7β-HSDH from *Collinsella aerofaciens* DSM 3979;

c) Stereoselective reduction of the 7-carbonyl group of 7-keto-LCA to a 7β-hydroxy group;

d) pH optimum for the oxidation of UDCA in the range from pH 8.5 to 10.5, in particular 9 to 10;

e) pH optimum for the reduction of DHCA and 7-keto-LCA in the range from pH 3.5 to 6.5, in particular at pH 4 to 6, whereby there is surprisingly the possibility of influencing oxidative (of feature d)) and reductive processes by selection of the pH;

f) at least one kinetic parameter from the following table for at least one of the substances/cofactors named there; in the range of ±20%, in particular ±10%, ±5%, ±3% ±2% or ±1% around the respective value specifically named in the following table.

| | $K_m$ (μM) | $V_{max}$ (U/mg protein)[b] | $k_{cat}$ (1 μmol/(μmol × min)) |
|---|---|---|---|
| NADP+[c] | 5.32 | 30.58 | 944.95 |
| NADPH[c] | 4.50 | 33.44 | 1033.44 |
| UDCA | 6.23 | 38.17 | 1179.39 |
| 7-keto-LCA | 5.20 | 30.77 | 950.77 |
| DHCA | 9.23 | 28.33 | 875.35 |
| NAD+ | —[a] | — | traces |
| NADH | — | — | traces |

[a] could not be determined owing to the very low activity
[b] 1 U = 1 μmol/min
[c] whereby the enzyme according to the invention differs markedly from the 7B-HSDH enzyme from *C. aerofaciens* ATCC25986 described by Hirano et al (see above), for which markedly lower $K_M$ and $V_{max}$ values (0.4 and 0.2 respectively) were described and no activity for NADPH was measured.

g) Phylogenetic sequence relatedness of the prokaryotic 7β-HSDH from *Collinsella aerofaciens* DSM 3979 related to the animal 11β-HSDH subgroup, comprising *Cavia porcellus*, *Homo sapiens* and *Mus musculus*.

For example a 7β-HSDH according to the invention displays the following properties or combinations of properties; a); b); a) and b); a) and/or b) and c); a) and/or b) and c) and d); a) and/or b) and c) and d) and e); a) and/or b) and c) and d) and e) and f)).

2. The 7β-HSDH or functional equivalent derived therefrom as stated in embodiment 1, which unlike the 7β-HSDH enzyme from C. aerofaciens ATCC25986 described by Hirano et al (see above) catalyzes
a) the stereospecific reduction (hydrogenation) of a 7-ketosteroid to the corresponding 7β-hydroxysteroid, and/or
b) the regiospecific hydrogenation (reduction) of a ketosteroid containing a keto group in the 7-position and at least one further keto group on the steroid skeleton to the corresponding 7β-hydroxysteroid, such as in particular of dehydrocholic acid (DHCA) in the 7-position to the corresponding 3,12-diketo-7β-cholanic acid, is for example NADPH-dependent.

3. A 7β-HSDH with an amino acid sequence according to SEQ ID No.: 2 (Accession No.: ZP_01773061) or a sequence derived therefrom with an identity of a least 60%, such as for example at least 65, 70, 75, 80, 85, or 90, such as for example at least 91, 92, 93, 94, 95, 96, 97, 98, 99 or 99.5% to this sequence; optionally additionally characterized by one of the following properties or combinations of properties; a); b); a) and b); a) and/or b) and c); a) and/or b) and c) and d); a) and/or b) and c) and d) and e); a) and/or b) and c) and d) and e) and f) according to the above definition.

4. A nucleic acid sequence coding for a 7β-HSDH according to the definition as stated in one of the previous embodiments, such as for example according to SEQ ID No.:1 (Accession No.: NZ_AAVN02000010, region: 52005 . . . 52796)

5. An expression cassette, comprising a nucleic acid sequence as stated in embodiment 4 under the genetic control of at least one regulative nucleic acid sequence.

6. A vector, comprising at least one expression cassette as stated in embodiment 5.

7. A recombinant microorganism which bears at least one nucleic acid sequence as stated in embodiment 4 or at least one expression cassette as stated in embodiment 5 or is transformed with at least one vector as stated in embodiment 6.

8. A method for the production of a 7β-HSDH as stated in one of embodiments 1 to 3, wherein a microorganism as stated in embodiment 7 is cultured and the 7β-HSDH expressed is isolated from the culture.

9. A method for the enzymatic synthesis of 7β-hydroxysteroids, wherein the corresponding 7-ketosteroid is converted in the presence of a 7β-HSDH according to the definition in one of embodiments 1 to 4, and at least one reduction product formed is optionally isolated from the reaction system.

10. The method as stated in embodiment 9, wherein the ketosteroid to be reduced is selected from
7-keto-lithocholic acid (7-keto-LCA),
7,12-diketo-lithocholic acid (7,12-diketo-LCA) and
the derivatives thereof, such as in particular a salt, amide or alkyl ester of the acid.

11. The method as stated in embodiment 10, wherein DCHA or a derivative thereof is converted to 3,12-diketo-7β-cholanic acid or to the corresponding derivative; or 7-keto-LCA or a derivative thereof is converted to ursodeoxycholic acid (UDCA) or to the corresponding derivative; or
7,12-diketo-LCA or a derivative thereof is converted to 12-keto-ursodeoxycholic acid (12-keto-UDCA).

12. The method as stated in one of embodiments 9 to 11, wherein the reduction takes place in the presence (and with consumption) of NAD(P)H.

13. A method for the enzymatic oxidation of 7β-hydroxysteroids, wherein the hydroxysteroid is reacted in the presence of a 7β-hydroxysteroid dehydrogenase according to the definition in one of embodiments 1 to 3, and an oxidation product formed is optionally isolated from the reaction system.

14. The method as stated in embodiment 13, wherein the 7β-hydroxysteroid is 3,12-diketo-7β CA or a derivative thereof, such as in particular a salt, amide or alkyl ester.

15. The method as stated in one of embodiments 13 and 14, wherein the oxidation takes place in the presence (and with consumption) of NAD(P)$^+$.

16. The method as stated in one of embodiments 12 and 15, wherein the redox equivalents consumed are electrochemically or enzymatically regenerated, in particular in situ.

17. The method as stated in embodiment 16, wherein consumed NAD(P)H is regenerated by coupling with an NAD(P)H-regenerating enzyme selected from an NAD(P)H dehydrogenase and in particular an alcohol dehydrogenase (ADH), in particular in situ.

18. The method as stated in embodiment 17, wherein the NAD(P)H-regenerating enzyme is selected from natural or recombinant, isolated or enriched
a) alcohol dehydrogenases (ADH; EC.1.1.1.2) and
b) functional equivalents derived therefrom (in particular functional domains).

19. A method for the production of ursodesoxycholic acid (UDSA) of the formula (1)

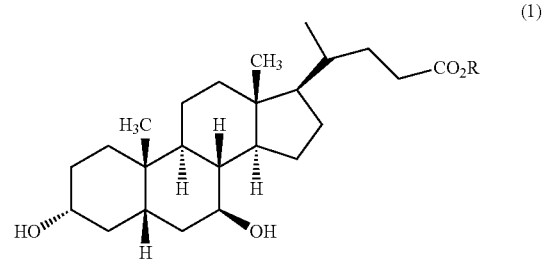

wherein
R stands for alkyl, $NR^1R^2$, H, an alkali metal ion or $N(R^3)_4{}^+$, wherein the residues $R^3$ are the same or different and stand for H or alkyl,
wherein
a) optionally a cholic acid (CA) of the formula (2)

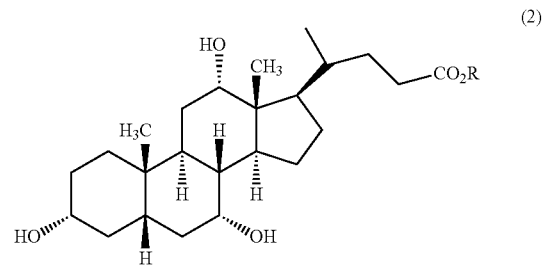

wherein R has the aforesaid meanings, is chemically oxidized to the dehydrocholic acid (DHCA) of the formula (3)

(3)

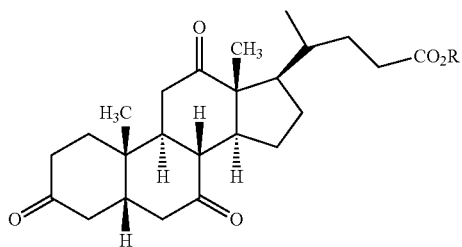

wherein R has the aforesaid meanings;

b) DHCA in the presence of at least one 7β-HSDH according to the definition in one of embodiments 1 to 3 is NADPH-dependently reduced to the 3,12-diketo-7β-cholanic acid (3,12-diketo-7β-CA) of the formula (4)

(4)

c) 3,12-diketo-7β-CA in the presence of at least one 3α-hydroxysteroid dehydrogenase (3α-HSDH) is NADPH-dependently or NADH-dependently (depending on the type of 3α-HSDH used) reduced to the corresponding 12-keto-ursodesoxycholic acid (12-keto-UDCA) of the formula (5)

(5)

wherein R has the aforesaid meanings and next d) 12-keto-UDCA of the formula (5) is chemically reduced to UDCA; and e) the reaction product is optionally further purified.

20. The method as stated in embodiment 19, wherein the steps b) and/or c) are performed in the presence of reduction equivalents (NADPH and/or NADH).

21. The method as stated in one of embodiments 19 and 20, wherein the steps b) and/or c) are coupled with an (in particular enzymatic) cofactor regeneration step.

22. The method as stated in embodiment 21 or 22, wherein step c) is coupled with a cofactor regeneration step, in particular in situ, in which depending on the type of 3α-HSDH used, NADH is regenerated by formate dehydrogenase (FDH) with consumption of formate (and formation of gaseous $CO_2$); or in which NADPH is regenerated by alcohol dehydrogenase (ADH) with consumption of a sacrificial alcohol (in particular isopropanol and formation of acetone) and wherein optionally the removal of acetone from the reaction equilibrium is promoted (e.g. by raising the temperature).

23. The method as stated in embodiment 21 or 22, wherein step c) is coupled with a cofactor regeneration step, in particular in situ, in which depending on the type of 3α-HSDH used, NADH is regenerated by formate dehydrogenase (FDH) with consumption of formate (and formation of gaseous $CO_2$); or in which NADPH is regenerated by alcohol dehydrogenase (ADH) with consumption of a sacrificial alcohol (in particular isopropanol and formation of acetone) and wherein optionally the removal of acetone from the reaction equilibrium is promoted (e.g. by raising the temperature).

24. The method as stated in one of embodiments 8 to 23, wherein the reaction is performed with at least one of the enzymes involved in immobilized form.

25. A bioreactor containing a 7β-hydroxysteroid dehydrogenase as stated in one of embodiments 1 to 3 in immobilized form.

FURTHER EMBODIMENTS OF THE INVENTION

1. General Definitions and Abbreviations Used

In the following table, the structural formulae, chemical names thereof and the abbreviations used are summarized in table form:

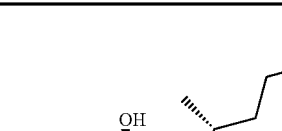

| Formula | Abbreviation | Chemical Name |
|---|---|---|
| Cholsäure | CA | Cholic acid |

-continued
| Formula | Abbreviation | Chemical Name |
|---|---|---|
| 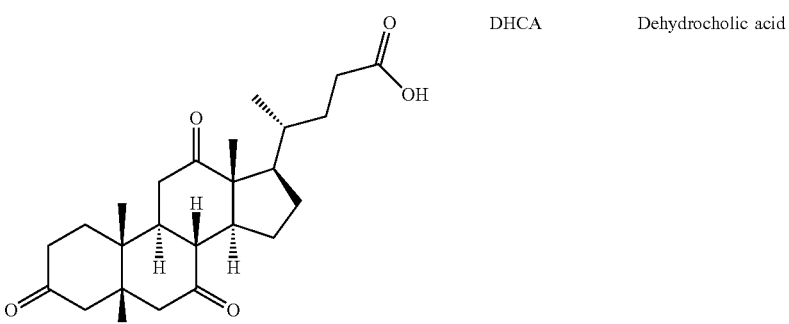 Dehydrocholsäure | DHCA | Dehydrocholic acid |
| 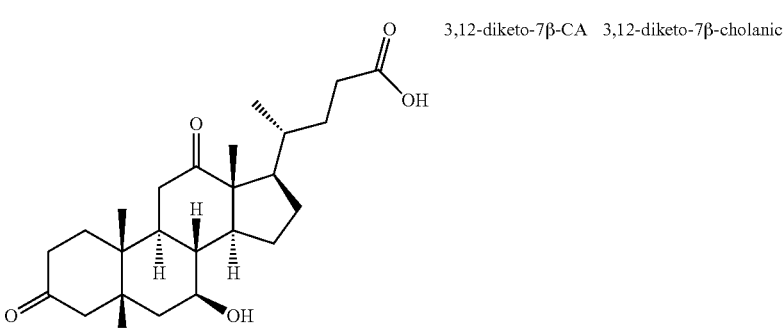 3,12-Diketo-7β-Cholansäure | 3,12-diketo-7β-CA | 3,12-diketo-7β-cholanic acid |
| 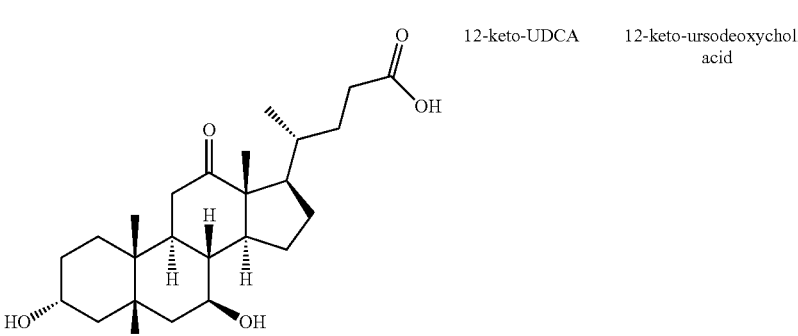 12keto-Ursodeoxycholsäure | 12-keto-UDCA | 12-keto-ursodeoxycholic acid |
| 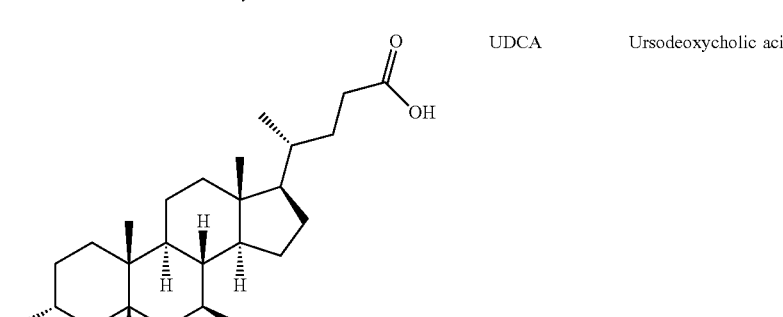 Ursodeoxycholsäure | UDCA | Ursodeoxycholic acid |

-continued

| Formula | Abbreviation | Chemical Name |
|---|---|---|
| Cholsäure-methylester | CA methyl ester | Cholic acid methyl ester |
| 3,7-Diacetyl-Cholsäure-methylester | 3,7-diacetyl-CA methyl ester | 3,7-diacetyl-cholic acid methyl ester* |
| 12-Keto-3,7-Diacetyl-Cholansäure-methylester | 12-keto-3,7-diacetyl-CA methyl ester | 12-keto-3,7-diacetyl-cholanic acid methyl ester* |
| Chenodeoxycholsäure | CDCA | Chendodeoxycholic acid |

-continued

| Formula | Abbreviation | Chemical Name |
|---|---|---|
| [structure: 7-Keto-Lithocholsäure] | 7-keto-LCA | 7-keto-lithocholic acid |
| [structure: 7,12-Diketo-Lithocholsäure] | 7,12-diketo-LCA | 7,12-diketo-lithocholic acid |
| [structure: 12-Keto-Chenodeoxycholsäure] | 12-keto-CDCA | 12-keto-chenodeoxycholic acid |

Unless otherwise stated, the term "7β-HSDH" designates a dehydrogenase enzyme which catalyzes at least the stereospecific and/or regiospecific reduction of DHCA to 3,12-diketo-7β-CA in particular with stoichiometric consumption of NADPH, and optionally the corresponding reverse reaction. Here the enzyme can be a natural or recombinantly produced enzyme. The enzyme in principle be present mixed with cellular, such as for example protein impurities, but preferably in pure form. Suitable detection methods are for example described in the experimental section below or known from the literature (e.g. *Characterization of NADP-Dependent 7 β-hydroxysteroid dehydrogenases from Peptostreptococcus productus and Eubacterium aerofaciens.* S Hirano and N Masuda. Appl Environ Microbiol. 1982; wherein however there no 7β-HSDH from *Eubacterium aerofaciens* which catalyzes the reduction of 7-keto groups could be detected). Enzymes with this activity are classified under the EC number 1.1.1.201.

Unless otherwise stated, the term "3α-HSDH" designates a dehydrogenase enzyme which catalyzes at least the stereospecific and/or regiospecific reduction of 3,12-diketo-7β CA to 12-keto-UDCA, in particular with stoichiometric consumption of NADH and/or NADPH, and optionally catalyzes the corresponding reverse reaction. Suitable detection methods are for example described in the experimental section below or known from the literature. Suitable enzymes are for example obtainable from *Comanomonas testosteroni* (e.g. ATCC11996). An NADPH-dependent 3α-HSDH is for example known from the rodents and is also usable. (Cloning and sequencing of the cDNA for rat liver 3 alpha-hydroxysteroid/dihydrodiol dehydrogenase, J E Pawlowski, M Huizinga and T M Penning, May 15, 1991 The Journal of Biological Chemistry, 266, 8820-8825). Enzymes with this activity are classified under the EC number 1.1.1.50.

According to the invention, a "pure form" or a "pure" or "essentially pure" enzyme is understood to mean an enzyme with a purity of more than 80, preferably more than 90, in particular more than 95, and above all more than 99 wt. %, based on the total protein content, determined by means of normal protein estimation methods, such as for example the biuret method or the protein estimation after Lowry et al. (see description in R. K. Scopes, Protein Purification, Springer Verlag, New York, Heidelberg, Berlin (1982)).

A "redox equivalent" is understood to mean a small molecule organic compound usable as an electron donor or electron acceptor, such as for example nicotinamide derivatives such as $NAD^+$ and $NADH^+$ or the reduced forms thereof NADH and NADPH respectively. $NAD(P)^+$ here stands $NAD^+$ and/or $NADP^+$ and NAD(P)H here stands for NADH and/or NADPH.

According to the invention, a "cholic acid compound" is understood to mean compounds with the basic carbon skeleton, in particular the steroid structure of cholic acid and the presence of keto and/or hydroxy or acyloxy groups at ring position 7 and optionally the ring positions 3 and/or 12.

A compound of a specific type, such as for example a "cholic acid compound" or an "ursodesoxycholic acid compound" is in particular also understood to mean derivatives of the underlying starting compound (such as for example cholic acid or ursodesoxycholic acid).

Such derivatives include "salts", such as for example alkali metal salts such as lithium, sodium and potassium salts of the compounds; and ammonium salts, where an ammonium salt is understood to include the $NH_4^+$ salt and those ammonium salts wherein at least one hydrogen atom can be replaced by a $C_1$-$C_6$ alkyl residue. Typical alkyl residues are in particular $C_1$-$C_4$ alkyl residues, such as methyl, ethyl, n- or i-propyl-, n-, sec- or tert-butyl, and n-pentyl and n-hexyl and the singly or multiply branched analogs thereof.

"Alkyl ester" compounds according to the invention are in particular low alkyl esters, such as for example $C_1$-$C_6$ alkyl esters. As non-limiting examples, methyl-, ethyl-, n- or i-propyl-, n-, sec- or tert-butyl esters, or longer chain esters, such as for example n-pentyl- and n-hexyl ester and the singly or multiply branched analogs thereof, can be named.

"Amides" are in particular conversion products of acids according to the invention with ammonia or primary or secondary monoamines. Such amines are for example mono- or di-$C_1$-$C_6$ alkyl monoamines, wherein the alkyl residues can mutually independently be optionally further substituted, for example by carboxy, hydroxy, halogen (such as F, Cl, Br or I), nitro and sulfonate groups.

"Acyl groups" according to the invention are in particular non-aromatic groups with 2 to 4 carbon atoms, such as for example acetyl, propionyl and butyryl, and aromatic groups with an optionally substituted mononuclear aromatic ring, wherein suitable substituents are for example selected from hydroxy, halogen (such as F, Cl, Br or I), nitro- and $C_1$-$C_6$ alkyl groups, such as for example benzoyl or toluoyl.

The hydroxysteroid compounds used or produced according to the invention, such as for example cholic acid, ursodesoxycholic acid, 12-keto-chenodesoxycholic acid, chenodesoxy-cholic acid and 7-keto-lithocholic acid can be used in the method according to the invention in stereoisomerically pure form or mixed with other stereoisomers or obtained therefrom. Preferably, however, the compounds used or prepared are used or isolated in essentially stereoisomerically pure form.

According to the invention, an "immobilization" is understood to mean the covalent or non-covalent binding of a biocatalyst used according to the invention, such as for example an 7β-HSDH to a solid, i.e. essentially insoluble in the surrounding liquid medium, support material.

2. Proteins

The present invention is not limited to the specifically disclosed proteins or enzymes with 7β-HSDH activity or 3α-HSDH activity, but rather also extends to functional equivalents thereof.

In the context of the present invention, "functional equivalents" or analogs of the specifically disclosed enzymes are polypeptides different therefrom, which moreover possess the desired biological activity, such as for example 7β-HSDH activity.

Thus for example "functional equivalents" is understood to mean enzymes which in the test for 7β-HSDH activity used display an activity of an enzyme comprising an amino sequence defined herein higher or lower by at least 1%, such as for example at least 10% or 20%, such as for example at least 50% or 75% or 90%. Apart from this, functional equivalents are preferably stable between pH 4 to 11 and advantageously have a pH optimum in a range from pH 4 to 6 or pH 6 to 10, such as for example 8.5 to 9.5, and a temperature optimum in the range from 15° C. to 80° C. or 15° C. to 40° C., 20° C. to 30° C. or 20° C. to 70° C., such as for example about 45 to 60° C. or about 50 to 55° C.

The 7β-HSDH activity can be detected by means of various known tests. Without being limited thereto, a test with use of a reference substrate, such as for example CA or DHCA, under standardized conditions as defined in the experimental section, may be mentioned.

According to the invention, "functional equivalents" is understood also in particular to mean "mutants" which in at least one sequence position of the aforesaid amino acid sequences have an amino acid other than that specifically named but nonetheless have one of the aforesaid biological activities. Thus "functional equivalents" include the mutants obtainable by one or more, such as for example 1, 2, 3, 4, 5, 6, 7, 8, 9, 10, 11, 12, 13, 14 or 15, amino acid additions, substitutions, deletions and/or inversions, where said changes can occur in any sequence position, so long as they lead to a mutant with the property profile according to the invention. In particular, there is also functional equivalence when the reactivity pattern between mutants and unchanged polypeptide qualitatively coincide, i.e. for example the same substrates are converted at different rates. Examples of suitable amino acid substitutions are summarized in the following table:

| Original Residue | Examples of Substitution |
| --- | --- |
| Ala | Ser |
| Arg | Lys |
| Asn | Gin; His |
| Asp | Glu |
| Cys | Ser |
| Gin | Asn |
| Glu | Asp |
| Gly | Pro |
| His | Asn; Gin |
| Iie | Leu; Val |
| Leu | Iie; Val |
| Lys | Arg; Gin; Glu |
| Met | Leu; He |
| Phe | Met; Leu; Tyr |
| Ser | Thr |
| Thr | Ser |

| Original Residue | Examples of Substitution |
|---|---|
| Trp | Tyr |
| Tyr | Trp; Phe |
| Val | Iie; Leu |

"Precursors" of the polypeptides described and "functional derivatives" and "salts" of the polypeptides are also "functional equivalents" in the above sense.

Here "precursors" are natural or synthetic precursors of the polypeptides with or without the desired biological activity.

The expression "salts" is understood to mean both salts of carboxyl groups and also acid addition salts of amino groups of the protein molecules according to the invention. Salts of carboxyl groups can be produced in a manner known per se and comprise inorganic salts such as for example sodium, calcium, ammonium, iron and zinc salts and salts with organic bases such as for example amines, such as triethanolamine, arginine, lysine, piperidine and the like. Acid addition salts, such as for example salts with mineral acids such as hydrochloric acid or sulfuric acid and salts with organic acids such as acetic acid and oxalic acid are also subjects of the invention.

"Functional derivatives" of polypeptides according to the invention can also be produced on functional amino acid side groups or on the N- or C-terminal ends thereof by known techniques. Such derivatives for example comprise aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also include polypeptides which are accessible from other organisms, and naturally occurring variants. For example, through sequence comparison zones of homologous sequence regions can be identified and equivalent enzymes determined on the basis of the specific stipulations of the invention.

"Functional equivalents" also include fragments, preferably individual domains or sequence motifs, of the polypeptides according to the invention, which for example display the desired biological function.

In addition, "functional equivalents" are fusion proteins which have one of the aforesaid polypeptide sequences or functional equivalents derived therefrom and at least one further, functionally different therefrom, heterologous sequence in functional N- or C-terminal linkage (i.e. without mutual functional impairment of the fusion protein parts). Non-limiting examples of such heterologous sequences are for example signal peptides, histidine anchors or enzymes.

According to the invention, homologs to the specifically disclosed proteins are also comprised with "functional equivalents". These possess at least 60%, preferably at least 75% in particular at least 85%, such as for example 90, 91, 92, 93, 94, 95, 96, 97, 98 or 99%, homology (or identity) to one of the specifically disclosed amino acid sequences, calculated according to the algorithm of Pearson and Lipman, Proc. Natl. Acad, Sci. (USA) 85(8), 1988, 2444-2448. A percentage homology or identity of a homologous polypeptide according to the invention means in particular percentage identity of the amino acid residues based on the overall length of one of the amino acid sequences specifically described herein.

The percentage identity values can also be determined on the basis of BLAST alignments, algorithm blastp (protein-protein BLAST), or by application of the clustal adjustments stated below.

In the case of a possible protein glycosylation, according to the invention "functional equivalents" include proteins of the type indicated above in deglycosylated or glycosylated form and modified forms obtained by alteration of the glycosylation pattern.

Homologs of the proteins or polypeptides according to the invention can be created by mutagenesis, e.g. by point mutation, elongation or truncation of the protein.

Homologs of the proteins according to the invention can be identified by screening of combinatorial banks of mutants, such as for example truncation mutants. For example, a variegated bank of protein variants can be created by combinatorial mutagenesis at the nucleic acid level, such as for example by enzymatic ligation of a mixture of synthetic oligonucleotides. There are a large number of methods which can be used for the production of banks of potential homologs from a degenerated oligonucleotide sequence. The chemical synthesis of a degenerated gene sequence can be performed in a DNA synthesizer, and the synthetic gene can then be ligated into a suitable expression vector. The use of a degenerated gene set enables the provision of all sequences in a mixture which code for the desired set of potential proteins. Methods for the synthesis of degenerated oligonucleotides are known to those skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the state of the art, several techniques are known for the screening of gene products of combinatorial banks which have been produced by point mutation or truncation, and for the screening of cDNA banks for gene products with a selected property. These techniques can be adapted for the rapid screening of the gene banks which have been created by combinatorial mutagenesis of homologs according to the invention. The most commonly used techniques for the screening of large gene banks which are subjected to a high throughput analysis comprise the cloning of the gene bank into replicable expression vectors, transformation of the suitable cells with the resulting vector bank and expression of the combinatorial genes under conditions under which the detection of the desired activity facilitates the isolation of the vector which encodes the gene the product whereof was detected. Recursive ensemble mutagenesis (REM), a technique which increases the incidence of functional mutants in the banks, can be used in combination with the screening tests in order to identify homologs (Arkin and Yourvan (1992) PNAS 89:7811-7815; Delgrave et al. (1993) Protein Engineering 6(3):327-331).

3. Nucleic Acids and Constructs 3.1 Nucleic Acids

Also a subject of the invention are nucleic acid sequences which code for an enzyme with 7β-HSDH or 3α-HSDH activity.

The present invention also relates to nucleic acids with a defined degree of identity to the specific sequences described herein.

"Identity" between two nucleic acids is understood to mean the identity of the nucleotides over the whole nucleic acid length in question, in particular the identity which is calculated by comparison by means of Vector NTI Suite 7.1

Software from Informax (USA) with use of the Clustal method (Higgins D G, Sharp P M. Fast and sensitive multiple sequence alignments on a microcomputer. Comput Appl. Biosci. 1989 April; 5(2):151-1) with adjustment of the following parameters:

Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively to this, the identity can also be determined after Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, as per the url: http://www.ebi.ac.uk/Tools/clustalw/indexhtml# and with the following parameters:

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All nucleic acid sequences mentioned herein (single and double strand DNA and RNA sequences, such as for example cDNA and mRNA) are producible in a manner known per se by chemical synthesis from the nucleotide building blocks, for example by fragment condensation of individual overlapping, complementary nucleic acid building blocks of the double helix. The chemical synthesis of oligonucleotides can for example be effected in known manner by the phosphoamidite method (Voet, Voet, $2^{nd}$ Edition, Wiley Press New York, pages 896-897). The attachment of synthetic oligonucleotides and filling of gaps by means of the Klenow fragment of DNA polymerase and ligation reactions and general cloning methods are described in Sambrook et al. (1989), Molecular Cloning: A laboratory manual, Cold Spring Harbor Laboratory Press.

Also a subject of the invention are nucleic acid sequences (single and double strand DNA- and RNA sequences, such as for example cDNA and mRNA) coding for one of the above polypeptides and functional equivalents thereof which are for example accessible with the use of artificial nucleotide analogs.

The invention relates both to isolated nucleic acid molecules which code for polypeptides or proteins according to the invention or biological active sections thereof, and also nucleic acid fragments, which can for example be used for utilization as hybridization probes or primers for the identification or amplification coding nucleic acids according to the invention.

The nucleic acid molecules according to the invention can also contain untranslated sequences from the 3' and/or 5' end of the coding gene region.

The invention further includes the nucleic acid molecules complementary to the specifically described nucleotide sequences or a section thereof.

The nucleotide sequences according to the invention enable the creation of probes and primers which are usable for the identification and/or cloning of homologous sequences in other cell types and organisms. Such probes or primers usually comprise a nucleotide sequence region which under "stringent" conditions (see below) hybridizes to at least about 12, preferably at least about 25, such as for example about 40, 50 or 75 consecutive nucleotides of a sense strand of a nucleic acid sequence according to the invention or a corresponding antisense strand.

An "isolated" nucleic acid molecule is separated from other nucleic acid molecules which are present in the natural source of the nucleic acid and can moreover be essentially free from other cellular material or culture medium if it is produced by recombinant techniques or be free from chemical precursors or other chemicals if it is chemically synthesized.

A nucleic acid molecule according to the invention can be isolated by means of standard molecular biology techniques and the sequence information provided according to the invention. For example, cDNA can be isolated from a suitable cDNA bank by using one of the specifically disclosed complete sequences or a section thereof as a hybridization probe and standard hybridization techniques (as for example described in Sambrook, J., Fritsch, E. F. and Maniatis, T. Molecular Cloning: A Laboratory Manual. $2^{nd}$ Edn., Cold Spring Harbor Laboratory, Cold Spring Harbor Laboratory Press, Cold Spring Harbor, N.Y., 1989). Moreover, a nucleic acid molecule comprising one of the disclosed sequences or a section thereof can be isolated by a polymerase chain reaction wherein the oligonucleotide primers which were created on the basis of this sequence are used. The nucleic acid thus amplified can be cloned into a suitable vector and characterized by DNA sequence analysis. Further, the oligonucleotides according to the invention can be produced by standard synthesis methods, e.g. with an automatic DNA synthesizer.

Nucleic acid sequences according to the invention or derivatives thereof, homologs or parts of these sequences can for example be isolated from other bacteria for example with usual hybridization methods or the PGR technique, e.g. via genomic or cDNA banks. These DNA sequences hybridize under standard conditions with the sequences according to the invention.

"Hybridization" is understood to mean the ability of a poly- or oligonucleotide to bind to an almost complementary sequence under standard conditions, while under these conditions nonspecific bindings between non-complementary partners does not occur. For this, the sequences can be 90-100% complementary. The property of complementary sequences of being able to bind specifically to one another is for example exploited in the Northern or Southern blot technique or in the primer binding in PCR or RT-PCR.

For the hybridization, short oligonucleotides of the conserved regions are advantageously used. However, longer fragments of the nucleic acids according to the invention or the complete sequences can also be used for the hybridization. These standard conditions vary depending on the nucleic acid used (oligonucleotide, longer fragment or complete sequence) or depending on what type of nucleic acid DNA or RNA are used for the hybridization. Thus for example the melting temperatures for DNA:DNA hybrids lie ca. 10° C. lower than those of DNA:RNA hybrids of the same length.

Depending on the nucleic acid, standard conditions should for example be understood to mean temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide, such as for example 42° C. in 5×SSC, 50% formamide. Advantageously, the hybridization conditions for DNA:DNA hybrids lie at 0.1×SSC and temperatures between about 20° C. and 45° C., preferably between about 30° C. to 45° C. For DNA:RNA hybrids, the hybridization conditions advantageously lie at 0.1×SSC and temperatures between about 30° C. and 55° C., preferably between about 45° C. and 55° C. These stated temperatures for the hybridization are melting temperature values calculated by way of example for a nucleic acid with a length of ca. 100 nucleotides and a G+C content of 50% in the absence of formamide. The experimental conditions for the DNA hybridization are described in relevant textbooks of genetics, such as for example Sambrook et al., "Molecular Cloning", Cold Spring Harbor Laboratory, 1989, and can be calculated according to formulae known to those skilled in the art for example depending on the length of the nucleic acids, the nature of the hybrids or the G+C content. Further information on hybridization can be obtained by those skilled in the art from the following textbooks: Ausubel et al. (Eds.), 1985, Current Protocols in Molecular Biology, John Wiley & Sons, New York; Hames and Higgins (Eds.), 1985, Nucleic Acids Hybridization: A Practical Approach, IRL Press at Oxford University Press, Oxford; Brown (Ed.), 1991, Essential Molecular Biology: A Practical Approach, IRL Press at Oxford University Press, Oxford.

The "hybridization" can in particular be effected under stringent conditions. Such hybridization conditions are for example described in Sambrook, J., Fritsch, E. F., Maniatis, T., in: Molecular Cloning (A Laboratory Manual), $2^{nd}$ Edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are in particular understood to mean: incubation at 42° C. overnight in a solution consisting of 50% formamide, 5×SSC (750 mM NaCl, 75 mM trisodium citrate), 50 mM sodium phosphate (pH 7.6), 5×Denhardt solution, 10% dextran sulfate and 20 g/ml denatured, sheared salmon sperm DNA, followed by a filter washing step with 0.1×SSC at 65° C.

Also a subject of the invention are derivatives of the specifically disclosed or derivable nucleic acid sequences.

Thus further nucleic acid sequences according to the invention can be derived e.g. from SEQ ID No.:1 and differ therefrom through addition, substitution, insertion or deletion of individual or several nucleotides, but still code for polypeptides with the desired property profile.

Also included according to the invention are those nucleic acid sequences which contain so-called silent mutations or are altered according to the codon usage of a specific origin or host organism, compared to a specifically named sequence, and also such as naturally occurring variants thereof, such as for example splice variants or allelic variants.

Also subject matter are sequences obtainable by conservative nucleotide substitutions (i.e. the relevant amino acid is replaced by an amino acid of the same charge, size, polarity and/or solubility).

Also a subject of the invention are the molecules derived from the specifically disclosed nucleic acids by sequence polymorphisms. These genetic polymorphisms can exist between individuals within a population on account of natural variation. These natural variations usually cause a variance of 1 to 5% in the nucleotide sequence of a gene.

Derivatives of the nucleic acid sequence according to the invention with the sequence SEQ ID No.: 1 should for example be understood to mean allelic variants which display at least 60% homology at the derived amino acid level, preferably at least 80% homology and quite especially preferably at least 90% homology over the whole sequence region (concerning homology at the amino acid level, reference may be made to the above explanations). Over part regions of the sequences, the homologies can advantageously be higher.

Furthermore, derivatives should also be understood to mean homologs of the nucleic acid sequences according to the invention, in particular of SEQ ID No.: 1, for example fungal or bacterial homologs, truncated sequences or single strand DNA or RNA of the coding and non-coding DNA sequence. Thus for example at the DNA level homologs to the SEQ ID No.: 1 possess a homology of at least 40%, preferably of at least 60%, particularly preferably of at least 70%, quite especially preferably of at least 80% over the whole DNA region stated in SEQ ID No.: 1.

In addition, derivatives should be understood for example to mean fusions with promoters. The promoters which are inserted in front of the stated nucleotide sequences may be modified by at least one nucleotide exchange, at least one insertions, inversions and/or deletions, without however the functionality or effectiveness of the promoters being impaired. Furthermore, the effectiveness of the promoters can be increased by modification of their sequence, or they can be completely replaced by more effective promoters even from organisms of other species.

Methods for the creation of functional mutants are moreover known to those skilled in the art.

Depending on the technique used, those skilled in the art can introduce random or also targeted mutations into genes or also non-coding nucleic acid regions (which for example are important for the regulation of expression) and then create gene banks. The molecular biology methods necessary for this are known to those skilled in the art and for example described in Sambrook and Russell, Molecular Cloning. $3^{rd}$ Edition, Cold Spring Harbor Laboratory Press 2001.

Methods for the modification of genes and thus for the modification of the proteins coded by these have long been familiar to those skilled in the art, for example
- site-specific mutagenesis, in which single or several nucleotides of a gene are specifically replaced (Trower M K (Ed.) 1996; In vitro mutagenesis protocols. Humana Press, New Jersey),
- saturation mutagenesis, in which a codon for any amino acid can be replaced or inserted at any site in a gene (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1),
- the error-prone polymerase chain reaction (error-prone PCR), in which nucleotide sequences are mutated by incorrectly operating DNA polymerases (Eckert K A, Kunkel T A (1990) Nucleic Acids Res 18:3739);

passaging of genes in mutator strains, in which for example because of defective DNA repair mechanisms an increased mutation rate of nucleotide sequences occurs (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction, in which by repeated strand separation and reassembly full-length mosaic genes are finally created (Stemmer W P C (1994) Nature 370:389; Stemmer W P C (1994) Proc Natl Acad Sci USA 91:10747).

With the use of so-called directed evolution (described inter alia in Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Ed.) Manual of industrial microbiology and biotechnology. American Society for Microbiology) those skilled in the art can also create functional mutants in a directed manner and also on a large scale. Here, in a first step, gene banks of the proteins in question are first created, for which for example the aforesaid methods can be utilized. The gene banks are expressed in a suitable manner, for example by bacteria or by phage display systems.

The relevant genes of host organisms which express functional mutants with properties which largely correspond to the desired properties can be subjected to a further round of mutation. The steps of mutation and selection or screening can be iteratively repeated until the present functional mutants display the desired properties to an adequate extent. Through this iterative mode of operation, a limited number of mutations, such as for example 1 to 5 mutations, can be performed stepwise and assessed and selected for their influence on the relevant enzyme property. The selected mutant can then be subjected to a further mutation step in the same manner. The number of individual mutants to be tested can thereby be significantly reduced.

The results according to the invention yield important information with regard to the structure and sequence of the enzymes concerned, which is necessary in order specifically to generate further enzymes with desired modified properties. In particular, so-called "hot spots", i.e. sequence sections which are potentially suitable for modifying an enzyme property via the introduction of targeted mutations, can be defined.

3.2 Constructs

Also a subject of the invention are expression constructs containing a nucleic acid sequence coding for a polypeptide according to the invention under the genetic control of regulative nucleic acid sequences, and vectors comprising at least one of these expression constructs.

According to the invention, an "expression unit" is understood to mean a nucleic acid with expression activity which contains a promoter as defined herein and after functional linkage with a nucleic acid or a gene to be expressed regulates the expression, that is the transcription and the translation, of this nucleic acid or this gene. Therefore in this context reference is also made to a "regulative nucleic acid sequence". In addition to the promoter, other regulative elements, such as for example enhancers, can also be contained.

According to the invention, an "expression cassette" or "expression construct" is understood to mean an expression unit which is functionally linked with the nucleic acid to be expressed or the gene to be expressed. In contrast to an expression unit, an expression cassette thus includes not only nucleic acid sequences which regulate transcription and translation, but also the nucleic acid sequences which are to be expressed as protein as a result of the transcription and translation.

In the context of the invention, the terms "expression" or "overexpression" describe the production or increase of the intracellular activity of one or more enzymes in a microorganism which are encoded by the corresponding DNA. For this, for example a gene can be introduced into an organism, an existing gene be replaced by another gene, the copy number of the genes or the genes increased, a strong promoter used or a gene used which codes for a corresponding enzyme with a high activity and these measures can optionally be combined.

Preferably such constructs according to the invention contain a promoter 5' upstream from the respective coding sequence and a terminator sequence 3' downstream, and optionally other normal regulative elements, also operatively linked to the coding sequence.

According to the invention, a "promoter", a "nucleic acid with promoter activity" or a "promoter sequence" is understood to mean a nucleic acid which in functional linkage with a nucleic acid to be transcribed regulates the transcription of this nucleic acid.

In this context, a "functional" or "operative" linkage is understood to mean for example the sequential arrangement of one of the nucleic acids with promoter activity and a nucleic acid sequence to be transcribed and optionally further regulative elements, such as for example nucleic acid sequences which ensure the transcription of nucleic acids, and for example a terminator, such that each of the regulative elements can fulfill its function in the transcription of the nucleic acid sequence. For this, a direct linkage in the chemical sense is not absolutely necessary. Genetic control sequences, such as for example enhancer sequences, can also fulfill their function on the target sequence from more remote positions or even from other DNA molecules. Arrangements in which the nucleic acid sequence to be transcribed is positioned behind (i.e. at the 3' end) of the promoter sequence, so that both sequences are covalently bonded to one another, are preferable. Here the distance between the promoter sequence and the nucleic acid sequence to be transgenically expressed can be less than 200 base pairs, or less than 100 base pairs or less than 50 base pairs.

As well as promoters and terminators, targeting sequences, enhancers, polyadenylation signals, selectable markers, amplification signals, replication origins and the like can be mentioned as examples of further regulative elements. Suitable regulatory sequences are for example described in Goeddel, Gene Expression Technology: Methods in Enzymology 185, Academic Press, San Diego, Calif. (1990).

Nucleic acid constructs according to the invention comprise in particular sequence SEQ ID No.: 1 or derivatives and homologs thereof, and the nucleic acid sequences derivable therefrom which have advantageously been operatively or functionally linked with one or more regulation signals for controlling, e.g. increasing the gene expression.

In addition to these regulative sequences, the natural regulation of these sequences can still be present before the actual structural genes and optionally have been genetically modified, so that the natural regulation has been switched off and the expression of the genes increased. However, the nucleic acid construct can also be more simply structured, that is no additional regulation signals have been inserted before the coding sequence and the natural promoter with its regulation has not been removed. Instead of this, the natural regulation sequence is mutated so that no further regulation takes place and the gene expression is increased.

A preferable nucleic acid construct advantageously also contains one or more of the aforesaid "enhancer" sequences, functionally linked with the promoter, which enable increased expression of the nucleic acid sequence. Additional advantageous sequences can also be inserted at the 3' end of the DNA sequences, such as further regulatory elements or terminators. The nucleic acids according to the invention can be contained in the construct in one or more copies. In the construct, further markers, such as antibiotic resistances or auxotrophy complementing genes, can optionally also be contained for selection for the construct.

Examples of suitable regulating sequences are contained in promoters such as cos-, tac-, trp-, tet-, trp-tet-, lac-, lpp-lac-, lacI$^{q-}$ T7-, T5-, T3-, gal-, trc-, ara-, rhaP (rhaP$_{BAD}$) SP6-, lambda-P$_R$- or in the lambda-P$_L$ promoter, which are advantageously used in gram-negative bacteria. Further advantageous regulating sequences are for example contained in the gram-positive promoters amy and SPO2, and in the yeast or fungal promoters ADC1, MFalpha, AC, P-60, CYC1, GAPDH, TEF, rp28 and ADH. Artificial promoters can also be used for the regulation.

For expression in a host organism, the nucleic acid construct is advantageously inserted into a vector, such as for example a plasmid or a phage which enables optimal expression of the genes in the host. Apart from plasmids and phages, vectors should also be understood to mean all other vectors known to those skilled in the art, for example viruses such as SV40, CMV, baculovirus and adenovirus, transposons, IS elements, phasmids, cosmids, and linear or circular DNA. These vectors can be autonomously replicated in the host organism or chromosomally replicated. These vectors are a further embodiment of the invention.

Suitable plasmids are for example: in E. coli pET28a(+), pLG338, pACYC184, pBR322, pUC18, pUC19, pKC30, pRep4, pHS1, pKK223-3, pDHE19,2, pHS2, pPLc236, pMBL24, pI_G200, pUR290, pIN-III$^{113}$-B1, λgt11 or pBdCl, in Streptomyces pIJ 101, pβ364, pIJ702 or pIJ361, in Bacillus pUB110, pC194 or pBD214, in Corynebacterium pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. Said plasmids represent a small selection of the possible plasmids. Further plasmids are well known to those skilled in the art and can for example be taken from the book Cloning Vectors (Eds. Pouwels P. H. et al. Elsevier, Amsterdam-New York-Oxford, 1985, ISBN 0 444 904018).

In a further embodiment of the vector, the vector containing the nucleic acid construct according to the invention or the nucleic acid according to the invention can also advantageously be introduced into the microorganisms in the form of a linear DNA and integrated into the genome of the host organism via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences according to the specific "codon usage" used in the organism. The "codon usage" can easily be determined on the basis of computer assessments of other, known genes of the organism concerned.

The production of an expression cassette according to the invention is effected by fusion of a suitable promoter with a suitable coding nucleotide sequence and a terminator or poly-adenylation signal. For this, standard recombination and cloning techniques, as for example described in T. Maniatis, E. F. Fritsch and J, Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987) are used.

For expression in a suitable host organism, the recombinant nucleic acid construct or gene construct is advantageously inserted into a host-specific vector which enables optimal expression of the genes in the host. Vectors are well known to those skilled in the art and can for example be taken from "Cloning Vectors" (Pouwels P. H. et al., Eds., Elsevier, Amsterdam-New York-Oxford, 1985).

4. Microorganisms

Depending on the context, the term "microorganism" can be understood to mean the starting microorganism (wild type) or a genetically modified, recombinant microorganism or both.

By means of the vectors according to the invention, recombinant microorganisms are producible, which for example are transformed with at least one vector according to the invention and can be used for the production of the polypeptides according to the invention. Advantageously, the recombinant constructs according to the invention described above are introduced into a suitable host system and expressed. Here, common cloning and transfection methods, such as for example coprecipitation, protoplast fusion, electroporation, retroviral transfection and the like known to those skilled in the art are preferably used in order to bring said nucleic acids to expression in the expression system in question. Suitable systems are for example described in Current Protocols in Molecular Biology, F. Ausubel et al., Ed., Wiley Interscience, New York 1997, or Sambrook et al. Molecular Cloning: A Laboratory Manual. 2nd Edn., Cold Spring Harbor Laboratory, Cold Spring Harbor Laboratory Press, Cold Spring Harbor, N.Y., 1989.

As recombinant host organisms for the nucleic acid or the nucleic acid construct according to the invention, in principle all prokaryotic or eukaryotic organisms are possible. Advantageously, microorganisms such as bacteria, fungi or yeasts are used as host organisms. Advantageously, gram-positive or gram-negative bacteria, preferably bacteria of the families Enterobacteriaceae, Pseudomonadaceae, Rhizobiaceae, Streptomycetaceae or Nocardiaceae, particularly preferably bacteria of the genera Escherichia, Pseudomonas, Streptomyces, Nocardia, Burkholderia, Salmonella, Agrobacterium, Clostridium or Rhodococcus are used. Quite especially preferably, the genus and species is Escherichia coli. Further advantageous bacteria are moreover to be found in the group of the alpha protobacteria, beta protobacteria or gamma protobacteria.

The host organism or the host organisms according to the invention here preferably contain at least one of the nucleic acid sequences, nucleic acid constructs or vectors described in this invention which code for an enzyme with 7R-HSDH activity according to the above definition.

The organisms used in the method according to the invention are grown or cultured in a manner known to those skilled in the art depending on the host organism. Microorganisms are as a rule cultured in a liquid medium which contains a carbon source mostly in the form of sugars, a nitrogen source mostly in the form of organic nitrogen sources such as yeast extract or salts such as ammonium sulfate, trace elements such as iron, manganese and magnesium salts and optionally vitamins, at temperatures between 0° C. and 100° C., preferably between 10° C. to 60° C. with oxygen aeration. During this, the pH of the nutrient liquid can be kept at a fixed value, that is regulated during the culturing, or not. The culturing can be effected "batch"-wise, "semi batch"-wise or continuously. Nutrients can be provided at the start of the fermentation or fed in semicontinuously or continuously thereafter.

5. Production of UDCA $1^{st}$ Step: Chemical Conversion of CA to DHCA

The hydroxy groups of CA are oxidized to carbonyl group with chromic acid or chromates in acidic solution (e.g. $H_2SO_4$) in a manner known per se by the classical chemical route. As a result, DHCA is formed.

$2^{nd}$ Step: Enzymatic Conversion of DHCA to 12-keto-UDCA In aqueous solution, DHCA is specifically reduced by 3α-HSDH and 7β-HSDH to 12-keto-UDCA in the presence of NADPH or NADH respectively. The cofactor NADPH or NADH can be regenerated by an ADH or FDH from isopropanol or sodium formate respectively. The reaction proceeds under mild conditions. For example, the reaction can be effected at pH=4 to 9, 6 to 9 or 7 to 9, in-particular about pH=8 and at about 10 to 30, 25 to 25 or about 23° C.

$3^{rd}$ Step: Chemical Conversion of 12-keto-UDCA to UDCA

The 12-carbonyl group of 12-keto-UDCA is removed by Wolff-Kishner reduction in a manner known per se, and thereby UDCA is formed from 12-keto-UDCA. In the reaction, the carbonyl group is firstly converted to the hydrazone with hydrazine. Next the hydrazone is heated to 200° C. in the presence of a base (e.g. KOH), and thereby nitrogen is cleaved off and UDCA is formed.

6. Recombinant Production of HSDH

Also a subject of the invention are methods for the recombinant production of polypeptides according to the invention or functional, biologically active fragments thereof, wherein a polypeptide-producing microorganism is cultured, if necessary expression of the polypeptide is induced and this is isolated from the culture. The polypeptides can thus also be produced on a large industrial scale, if this is desired.

The microorganisms produced according to the invention can be cultured continuously or discontinuously in the batch process (batch culturing) or in the fed batch process or repeated fed batch process. A summary of known culturing methods can be found in the textbook by Chmiel (Bioprocess Technology 1. Introduction to bioprocess technology (Gustav Fischer Verlag, Stuttgart, 1991)) or in the textbook by Storhas (Bioreactors and peripheral devices (Vieweg Verlag, Braunschweig/Wiesbaden, 1994)).

The culture medium to be used must appropriately satisfy the needs of the strains in question. Descriptions of culture media of various microorganisms are contained in the handbook "Manual of Methods for General Bacteriology" from the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars such as mono-, di- or polysaccharides. Very good carbon sources are for example glucose, fructose, mannose, galactose, ribose, sorbose, ribulose, lactose, maltose, saccharose, raffinose, starch or cellulose. Sugars can also be added to the media via complex compounds such as molasses or other byproducts of sugar refining. It can also be advantageous to add mixtures of different carbon sources. Other possible carbon sources are oils and fats such as for example soya oil, sunflower oil, peanut oil and coconut fat, fatty acids such as for example palmitic acid, stearic acid or linolic acid, alcohols such as for example glycerin, methanol or ethanol and organic acids such as for example acetic acid or lactic acid.

Nitrogen sources are usually organic or inorganic nitrogen compounds or materials which contain these compounds. Examples of nitrogen sources include ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soya meal, soya protein, yeast extract, meat extract, and others. The nitrogen sources can be used singly or as a mixture.

Inorganic salt compounds which can be contained in the media include the chloride, phosphorus or sulfate salts of calcium, magnesium, sodium, cobalt, molybdenum, potassium, manganese, zinc, copper and iron.

As a sulfur source, inorganic sulfur-containing compounds such as for example sulfates, sulfites, dithionites, tetrathionates, thiosulfates and sulfides, but also organic sulfur compounds such as mercaptans and thiols, can be used.

As a phosphorus source, phosphoric acid, potassium dihydrogen phosphate or dipotassium hydrogen phosphate or the corresponding sodium-containing salts can be used.

Chelating agents can be added to the medium in order to hold the metal ions in solution. Particularly suitable chelating agents include dihydroxyphenols such as catechol or proto-catechuate, or organic acids such as citric acid.

The fermentation media used according to the invention usually also contain other growth factors, such as vitamins or growth promoters including for example biotin, riboflavin, thiamine, folic acid, nicotinic acid, pantothenate and pyridoxine. Growth factors and salts often derive from complex media components such as yeast extract, molasses, corn steep liquor and the like. Apart from this, suitable precursors can be added to the culture medium. The exact composition of the media compounds depends strongly on the particular experiment and is decided individually for each specific case. Information about media optimization is obtainable from the textbook "Applied Microbiol. Physiology, A Practical Approach" (Ed. P. M. Rhodes, P. F. Stanbury, IRL Press (1997) S. 53-73, ISBN 0 19 963577 3). Growth media can also be obtained from commercial suppliers, such as Standard 1 (Merck) or BHI (Brain heart infusion, DECO) and the like.

All media components are sterilized, either by heat (20 mins at 1.5 bar and 121° C.) or by sterile filtration. The components can either be sterilized together or if necessary separately. All media components can be present at the start of the culturing or optionally be added continuously or in batches.

The culture temperature normally lies between 15° C. and 45° C., preferably at 25° C. to 40° C. and can be kept constant or varied during the experiment. The pH of the medium should lie in the range from 5 to 8.5, preferably around 7.0. The pH for the culturing can be controlled during the culturing by addition of basic compounds such as sodium hydroxide, potassium hydroxide, ammonia or aqueous ammonia or acidic compounds such as phosphoric acid or sulfuric acid. To control foam development, antifoamants such as for example fatty acid esters can be used. To maintain the stability of plasmids, suitable selectively acting substances, such as for example antibiotics, can be added to the medium. In order to maintain aerobic conditions, oxygen or oxygen-containing gas mixtures, such as for example ambient air, are introduced into the culture. The culture temperature normally lies at 20° C. to 45° C. The culturing is continued until a maximum of the desired product has formed. This target is normally reached within 10 hours to 160 hours.

The fermentation broth is then further processed. As required, the biomass can be wholly or partly removed from the fermentation broth by separation methods, such as for example centrifugation, filtration, decantation or a combination of these methods, or be entirely left therein.

The cells can also, if the polypeptides are not secreted into the culture medium, be disintegrated and the product recovered from the lysate by known protein isolation methods. The cells can optionally be disintegrated by high frequency ultrasound, by high pressure, for example in a French press, by osmolysis, by the action of detergents, lytic enzymes or organic solvents, by homogenizers or by combination of several of the stated methods.

A purification of the polypeptides can be achieved by known chromatographic methods such as molecular sieve chromatography (gel filtration), such as Q-Sepharose chromatography, ion exchange chromatography and hydrophobic chromatography, and with other usual methods such as ultrafiltration, crystallization, salting out, dialysis and native gel electrophoresis. Suitable methods are for example described in Cooper, F. G., Biochemical Working Methods, Verlag Walter de Gruyter, Berlin, N.Y. or in Scopes, R., Protein Purification, Springer Verlag, N.Y., Heidelberg, Berlin.

For the isolation of the recombinant protein, it can be advantageous to use vector systems or oligonucleotides which lengthen the cDNA by certain nucleotide sequences and hence code for modified polypeptides or fusion proteins which for example serve for simpler purification. Such suitable modifications are for example so-called "tags" functioning as anchors, such as for example the modification known as the hexa-histidine anchor or epitopes which can be recognized as antigens by antibodies (described for example in Harlow, E. and Lane, D., 1988, Antibodies: A Laboratory Manual. Cold Spring Harbor (N.Y.) Press). These anchors can serve for the attachment of the proteins onto a solid support, such as for example a polymer matrix, which can for example be filled into a chromatography column, or can be used on a microtiter plate or on another support.

At the same time, these anchors can also be used for recognition of the proteins. In addition, for recognition of the proteins normal markers, such as fluorescent dyes, enzyme markers which form a detectable reaction product after reaction with a substrate, or radioactive markers, alone or in combination with the anchors for derivatization of the proteins can be used.

7. Enzyme Immobilization

The enzymes according to the invention can be used free or immobilized in the methods described herein. An immobilized enzyme is understood to mean an enzyme which is fixed onto an inert support. Suitable support materials and the enzymes immobilized thereon are known from EP-A-1149849, EP-A-1 069 183 and DE-OS 100193773 and from the literature references cited therein. In this regard, reference is made to the disclosure of these publications in its entirety. Among the suitable support materials are for example clays, clay minerals such as kaolinite, diatomaceous earth, perlite, silicon dioxide, aluminum oxide, sodium carbonate, calcium carbonate, cellulose powder, anion exchanger materials, and synthetic polymers such as polystyrene, acrylic resins, phenol formaldehyde resins, polyurethanes and polyolefins, such as polyethylene and polypropylene. The support materials are normally used for the production of the supported enzymes in a finely divided, particulate form, with porous forms being preferable. The particle size of the support material is usually not more than 5 mm, in particular not more than 2 mm (size distribution curve). Analogously, with use of the dehydrogenase as a whole cell catalyst, a free or immobilized form can be selected. Examples of support materials are Ca alginate, and carrageenan. Enzymes, like cells, can also be directly cross-linked with glutaraldehyde (crosslinking to CLEAs). Similar and other immobilization methods are for example described in J. Lalonde and A. Margolin "Immobilization of Enzymes" and in K. Drauz and H. Waldmann, Enzyme Catalysis in Organic Synthesis 2002, Vol. 111, 991-1032, Wiley-VCH, Weinheim.

Experimental Section

Unless otherwise stated, the cloning steps performed in the context of the present invention, such as for example restriction cleavages, agarose gel electrophoresis, purification of DNA fragments, transfer of nucleic acids onto nitrocellulose and nylon membranes, linkage of DNA fragments, transformation of microorganisms, culturing of microorganisms, proliferation of phages and sequence analysis of recombinant DNA can be performed as described in Sambrook et al. (1989) loc. cit.

1. GENERAL INFORMATION

Materials:

The genomic DNA from *Collinsella aerofaciens* DSM 3979 (ATCC 25986, former designation *Eubacterium aerofaciens*) was obtained from the German Collection for Microorganisms and Cell Cultures (DSMZ). UDCA and 7-keto-LCA are starting compounds known per se and described in the literature. All other chemicals were obtained from Sigma-Aldrich and Fluka (Germany). All restriction endonucleases, the T4 DNA ligase, the Taq DNA polymerase and isopropyl-3-D-1-thiogalactopyranoside (IPTG) were obtained from Fermentas (Germany).

Media:

LB medium, containing Trypton 10 g, yeast extract 5 g and NaCl 5 g per liter of medium.

Expression Vectors pET22b(+) and pET28a(+) (Novagen, Madison, Wis., USA).

Microorganisms

The *Escherichia, coli* strain DH5a (Novagen, Madison, Wis., USA) was proliferated at 37° C. in LB medium containing suitable antibiotics.

The *Escherichia coli* strain BL21(DE3) (Novagen, Madison, Wis., USA) was proliferated at 37° C. in LB medium containing suitable antibiotics, and after induction at $OD_{60}0=0.8$ with 0.5 mM IPTG was maintained at 25° C. and 140 Rpm.

Analytical Methods

1. Standard Conditions for 7β-HSDH Activity Determination

The reaction mixture contains a total volume of 1 ml:

| | |
|---|---|
| 880 µl | 50 mM potassium phosphate buffer, pH 8.0 |
| 10 µl | 10 mM UDCA (dissolved in water, pH 8) |
| 10 µl | enzyme solution (in buffer as above, in the range from 1 to 10 U/ml) |
| 100 µl | 1 mM NADP+ (in buffer as above) |

The increase in the extinction at 340 nm is measured and the activity is calculated as enzyme unit (U, i.e. µmol/min) using the molar extinction coefficient of $6.22\ mM^{-1} \times cm^{-1}$.

2. PROTEIN DETERMINATION BY BCA ASSAY

The samples were mixed with BCA reagent (from Interchim) and incubated at 37° C. for 45 mins. The protein content was determined at 562 nm against a calibration curve (BSA) in the concentration range of the assay used.

3. THIN LAYER CHROMATOGRAPHY 5 to 10 µg of sample were applied onto a TLC film Kieselgel 60 (Merck). Authentic substances were applied as the reference. One end of the TLC film was dipped in eluent until the mobile phase reaches the top. The TLC film was dried and developed with phosphomolybdic acid.

2. EXAMPLES

Production Example 1: Identification of 7β-HSDH Activity

The genomic DNA sequence of *Collinsella aerofaciens* ATCC 25986 was published at GenBank in 2007 by "Washington University Genome Sequencing Center" for the "human gut microbiome project". HSDHs are among the "Short-Chain dehydrogenases". Since the biochemical function of the "Short-Chain dehydrogenases" from *Collinsella aerofaciens* ATCC 25986 was not annotated in GenBank, 9 candidates were cloned into vector pET22b+ and then expressed in *E. coli* BL21 (DE3).

For this, 7β-HSDH coding sequences were PCR-amplified. The PCR products were obtained using the genomic DNA of *Collinsella aerofaciens* ATCC 25986 (DSM 3979) as template and the primers 5'-gqqaattc CATATGAACCTGAGGGAGAAGT A-3' (SEQ ID No.:3) and 5'-cccAAGCTTCTAGTCGCGGTAGAACGA-3' (SEQ ID No.:4). The NdeI and HindIII cleavage sites in the primer sequences are underlined. The PCR product was purified with PCR Purification Kit (Qiagen) and then cleaved with the enzymes NdeI and HindIII. The relevant vector was also cleaved with the NdeI and HindIII. The products were applied on to an agarose gel, separated, cut out from this and purified. The cleaved PCR product and the cleaved vector were ligated with T4 ligase. The ligation product was transformed into *E, coli* DH5a. The resulting vector (contains the gene of 7β-HSDH) was confirmed by sequencing and transformed into *E. coli* BL21(DE3) and induced with IPTG and expressed.

The expression was performed in 50 ml of LB medium. For the preparation of preculture, one colony on an LB agar plate was picked and incubated overnight at 37° C. and 160 Rpm in 5 ml of LB medium (contains relevant antibiotics) a. The 50 ml of LB medium (contains relevant antibiotics) was inoculated with 500 pi of preculture. The culture was incubated at 37° C. and 160 Rpm. Up to OD600 ca. 0.8, expression was induced by addition of 0.5 mM IPTG. After 6 hrs or one night, the cells were centrifuged down. The pellets were resuspended in 6 ml of potassium phosphate buffer (50 mM, pH 8, contains 0.1 mM PMSF) and disintegrated with ultrasound. The cell fragments were removed by centrifugation.

For the identification of 7β-HSDH activity the activity was tested by photometric methods. For this, enzyme and 0.1 mM of test substance (UDCA) in potassium phosphate buffer (50 mM, pH 8) were mixed in a 1 ml cuvette. After addition of NADPH(NADH) or $NADP^+$ ($NAD^+$), the degradation or formation of NAD(P)H was measured. One enzyme from the 9 candidates shows activity (60 U/ml) against UDCA in the presence of NADP\ but no activity against CA. The NADPH-dependent 7β-HSDH activity of this enzyme was identified.

In the photometric testing, the 7β-HSDH displayed the activity 60 U/ml against UDCA, activity 35 U/ml against 7-keto-LCA and activity 119 U/ml against DHCA in the presence of $NADP^+$ or NADPH. The activity against CA is not detectable.

The gene which codes for the 7β-HSDH was recloned in pET28a+ with His-Tag, in order to enable rapid purification. This 7β-HSDH with His-Tag was actively expressed in *E. coli* BL21(DE3) as was described above. The purification was performed with a Talon column. The column was first equilibrated with potassium phosphate buffer (50 mM, pH 8, with 300 mM NaCl). After the cell lysate had been loaded, the column was washed with potassium phosphate buffer (50 mM, pH 8, with 300 mM NaCl). The 7β-HSDH was eluted with potassium phosphate buffer (50 mM, pH 8, with 300 mM NaCl and 200 mM imidazole). The imidazole in the eluate was removed by dialysis. The purification yield was 76% with purity ca. 90%.

Conversion Example 1: Enzymatic Conversion of 7-keto-LCA by the 7β-HSDH

To check the biochemical function of the 7β-HSDH, a conversion of 7-keto-LCA by the 7β-HSDH was performed. The 20 ml conversion mixture contains 50 mM 7-keto-LCA (ca. 0.4 g), 5 U/ml 7β-HSDH and 0.05 mM $NADP^+$. For regeneration of NADPH, 4 U/ml ADH and 1% isopropanol was used (see Scheme 1). The reaction was performed in the fume cupboard at pH 8 and 24° C. with stirring. Since acetone evaporates faster than isopropanol, the reaction is shifted towards formation of UDCA. 1% isopropanol was again added after 24 hrs, 48 hrs and 72 hrs. The product was analyzed by TLC (Kieselgel 60, Merck, mobile phase petroleum ether and ethyl acetate 1:10, vol:vol). On TLC the product was compared with authentic references 7-keto-LCA, UDCA and CDCA. The TLC analysis shows that UDCA was formed from 7-keto-LCA by the 7β-HSDH. The enantiomer CDCA is not detectable on TLC.

Scheme 1: FIG. 1e is a schematic representation of reduction of 7-keto-LCA by the 7β-HSDH. The ADH regenerates the cofactor NADPH.

Conversion Example 2: Enzymatic Production of 12-keto-UDCA from DHCA by 7β-HSDH

To test the usability of the 7β-HSDH for production of 12-keto-UDCA from DHCA, a conversion of DHCA by the 7β-HSDH was performed. The 50 ml conversion mixture contains 50 mM DHCA (1 g), 5 U/ml 7β-HSDH and 0.05 mM $NADP^+$. For regeneration of NADPH,4 U/ml ADH and 1% isopropanol was used (see Scheme 2). The reaction was performed in the fume cupboard at pH 8 and 24° C. with stirring. Since acetone evaporates faster than isopropanol, the reaction is shifted towards formation of 3,12-diketo-7β-CA. In order to attain complete conversion, 1% isopropanol was again added after 24 hrs, 48 hrs and 72 hrs. The intermediate 3,12-diketo-7β-CA was analyzed by TLC. The reactant DHCA was no longer detectable on TLC (Kieselgel 60, Merck; mobile phase chloroform:methanol:acetic acid 10:1:0.08 vol:vol:vol).

Scheme 2: FIG. 1f is a schematic representation of reduction of DHCA by the 7β-HSDH. The ADH regenerates the cofactor NADPH.

Conversion Example 3: Enzymatic Conversion of 3,12-diketo-7β-CA to 12-keto-UDCA

The intermediate 3,12-diketo-7β-CA (prepared according to conversion example 2) was converted further to 12-keto-UDCA by a 3α-HSDH (SEQ ID Nos.:5 and 6) from *Comamonas testosteroni* (Mobus, E. and E. Maser, *Molecular cloning, overexpression, and characterization of steroid-inducible 3alpha-hydroxysteroid dehydrogenase/carbonyl reductase from Comamonas testosteroni. A novel member of the short-chain dehydrogenase/reductase superfamily*. J Biol Chem, 1998. 273(47): p. 30888-96). This 3α-HSDH requires cofactor NADH, which was regenerated by the FDH (see FIG. 4). 4 U/ml 3α-HSDH, 1 U/ml FDH (NADH-dependent, Codexis), 200 mM sodium formate and 0.05 mM $NAD^+$ were added to the reaction. After 40 hrs, the product was acidified to pH 2 with 2M HCl and extracted with 6 times 10 ml ethyl acetate. After evaporation, 1.07 g of product were obtained. The product 12-keto-UDCA was analyzed and confirmed by TLC and NMR. The 3alpha-HSDH was produced analogously to the production of 7R.-HSDH, but with the plasmid pET22b+, and used without further purification.

Figure 1G:
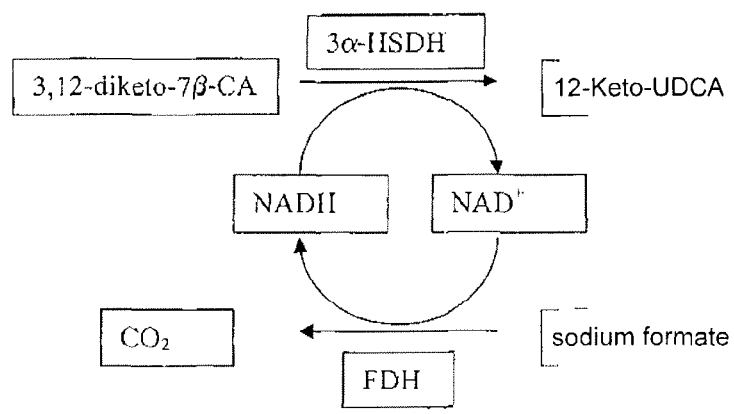
FIG. 1g is a schematic representation of reaction Scheme 3 for the reduction of 3,12-diketo-7β-CA by the 3α-HSDH.

Scheme 3: FIG. 1g is a schematic representation the reduction of 3,12-diketo-7β-CA by the 3α-HSDH. The FDH regenerates the cofactor NADH.

Conversion Example 4: Chemical Conversion of CA to DHCA 1320 l of glacial acetic acid are placed in a 2000 l stirred vessel and 110 kg (260 mol) of cholic acid (CA) dissolved therein. 422 l of sodium hypochlorite solution (2.3 molar) are metered into this solution at 20 to 40° C. and the reaction solution then further stirred for at least 1 hour for completion of the reaction. The dehydocholic acid (DHCA) is isolated in a yield of 100 kg (90%) by centrifugation.

Conversion Example 5: Chemical Conversion of 12-keto-UDCA to UDCA 105 g (0.258 mol) of 12-keto-UDCA are dissolved in 384 ml of triethylene glycol, 522 g (1.304 mol) of sodium hydroxide and 75.95 ml (1.563 mol) of hydrazine hydrate and slowly heated to 180° C. During this, the hydrazone is formed, which beyond 160° C. rearranges into the UDCA with liberation of nitrogen. For completion of the conversion, the reaction mixture is maintained at 180° C. for 8 hours. The reaction mixture is cooled below 100° C., and treated with 1500 ml of water. Next, the UDCA is precipitated by acidification with hydrochloric acid. The product is obtained in a yield of 96.2 g to 99.2 g (up to 95%-98%).

Production Example 2: Cloning, Expression and Purification of 7β-HSDH from *Collinsella aerofaciens* ATCC 25986 on Preparative Scale and Further Characterization of the Enzyme a) Cloning and Production of an Expression Construct The gene coding for 7/J-HSDH coding gene was once again amplified from the genomic DNA by PCR and with use of primers, as described above for Production Example 1:

The PCR product was once again purified as described above and digested with the restriction endonucleases NdeI and HindIII. The digested PCR product was once again purified and cloned into the pET-28a(+) vector using the T4 ligase, in order to create an expression vector. The resulting expression construct was then transformed into *E. coli* DH5a cells. The protein to be expected should have 20 amino acid residues comprising a signal peptide and an N-terminal 6×His-Tag and a thrombin cleavage site. The sequence of the inserted DNA was checked by sequencing.

b) Overexpression and Purification of 7β HSDH

*E. coli* BL21(DE3) was transformed with the expression construct. For this, the *E. coli* BL21(DE3) strain containing the expression construct was proliferated in LB medium (2×400 ml in 2 liter shaker bottles) containing 30 µ/ml kanamycin. The cells were harvested by centrifugation (10, 000×g, 15 mins, 4° C.). The pellet was resuspended in 20 ml of phosphate buffer (50 mM, pH 8, containing 0.1 mM PMSF). The cells were disintegrated with constant cooling by one-minute ultrasound treatment (40 W power, 40% interval and 1 min pause) with the use of a Sonifier 250 ultrasound device (Branson, Germany). The disintegration was repeated three times. The cell extract was centrifuged (22,000×g, 20 mins, 4° C.). The supernatant was loaded onto a Talon column (Clontech, USA) equilibrated with loading buffer (50 mM potassium phosphate, 300 mM NaCl, pH 8). The process was carried out at 24° C. Non-bound material was washed out by washing of the column with loading buffer (3 column volumes). Weakly binding protein was removed by washing with washing buffer (20 mM imidazole in the loading buffer; 3 column volumes). The His-Tag-7β-HSDH protein was eluted with elution buffer (200 mM imidazole in the loading buffer). The eluate was dialyzed overnight at 4° C. in a dialysis tube with a molecular exclusion limit of 5 kDa (Sigma, USA) in 2 liters of potassium phosphate buffer (50 mM, pH 8). Finally the sample was transferred into a new tube and stored at −20° C. for further analysis. The protein concentration was determined using a BCA test kit. (Thermo, USA) according to the manufacturer's instructions. In addition, the sample was analyzed by 12.5% SDS-PAGE and staining with Coomassie Brilliant Blue. The purity of the protein was determined by densitometry by means of Scion Image Beta 4.0.2 (Scion, USA).

c) Gel Filtration

Gel filtration was performed on a Pharmacia AKTA protein purification system in order to determine the molecular weight of 7β-HSDH. The purified enzyme was applied onto a Sephadex G-200 column which had previously been equilibrated with 50 mM Tris-HCl (pH 8) containing 200 mM sodium chloride. The protein was eluted with the same buffer at a flow rate of 1 ml/min. The molecular weight of 7β-HSDH was determined by comparison of its elution volume with that of protein standards (serum albumin (66 kDa), o-amylase from *Aspergillus oryzae* (52 kDa), trypsin from pig pancreas (24 kDa) and lysozyme from chicken egg (14.4 kDa)).

d) Enzyme Test and Kinetic Analysis

The reaction mixture for the enzyme test contained 50 µmol potassium phosphate (pH 8), 0.1 µmol NAD(P)H or NAD(P)\ substrate and protein in a total volume of 1 ml. The reaction mixture was contained in cuvettes with a light path length of 1 cm. The 7β-HSDH activity was determined by recording the change in the NAD(P)H concentration via the extinction at 340 nm by means of a spectrophotometer (Ultraspec 3000, Pharmacia Biotech, Great Britain). The enzyme activities were determined as enzyme units (U, i.e. µmol/min) using the molar extinction coefficient of 6.22 $mM^{-1} \times cm^{-1}$ at 25° C. Several different measurements with the variables substrate, coenzyme, concentration, pH, buffer and incubation temperature were performed. The kinetic constants were determined using standard methods.

e) Biotransformation of 7-keto-lithocholic Acid by the 7β-HSDH

The conversion of 7-keto-LCA by 7β-HSDH was performed in order to verify the biochemical function of 7β-HSDH. 0.4 g of 7-keto-LCA were suspended in 10 ml of potassium phosphate buffer (50 mM, pH 8) and the pH was adjusted to pH 8 by addition of 2M sodium hydroxide. 0.2 ml of isopropanol, 100 U of 7β-HSDH and 80 U of alcohol dehydrogenase (ADH-TE) from *Thermoanaerobacter ethanolicus* (kindly donated by Dr. K. Momoi, ITB University, Stuttgart) and 1 µmol $NADP^+$ were added. The same buffer was added, so as to obtain a total reaction volume of 20 ml. The reaction mixture was incubated at 24° C. and stirred for 24 hours. During this, NADPH was regenerated by means of ADH via the oxidation of 2-propanol. The product was acidified with 1 ml of 2M hydrochloric acid and extracted 5* with 5 ml of ethyl acetate. The organic solution was then distilled.

f) Chromatographic Product Determination

An HPLC analysis was performed on a column of the Purospher® STAR RP-18 type (Hitbar® RT 125-4 Pre-Packed Column, Purospher® STAR RP-18 endcapped, Merck, Germany), equipped with a precolumn of the LiChroCART® STAR RP18 type (endcapped, Merck, Germany) on an LC20AD HPLC system (Shimadzu, Japan) at a flow rate of 1 ml/min. The mobile phase consisted of two eluents, Eluent A contained acetonitrile and eluent B distilled water (pH 2.6, adjusted with orthophosphoric acid, 85%). The following gradient was used: A 35% (8 min)—35%-43% (1% $min^{-1}$)—43%-70% (1% $min^{-1}$)—70% (5 min)—70%-35% (17.5% $min^{-1}$)—35% (5 min); eluent A 65% (8 min)—65%-57% (1% $min^{-1}$)—57%-30% (1% $min^{-1}$)—30% (5 min)—30%-65% (17.5% $min^{-1}$)—65% (5 min). 20 µl sample (1 mg/ml) were analyzed. Authentic UDCA, 7-keto-LCA and CDCA were used at the same concentration as standards. The recording was performed by UV detection at 200 nm.

g) Sequence Alignment and Phylogenetic Analysis

Multiple sequence alignments were created using the Clustal X software (Thompson et al., 1997, Nucleic Acid Research 25: 4876-82) and modified using the Jalview-Software (Clamp et al., 2004, Bioinformatics 20:426-7). The phylogenetic tree was created using the program TreeView 1.6.6 (Roderic 2001, http://taxonomv.zoology.qIa.ac.uk/rod/rodhtmn.

h) Test Results:

1. Identification of 7β-HSDH Activity in a Preparative Biotransformation

To confirm the function of the enzyme, a biotransformation of 7-keto-LCA on the 10 ml scale was performed, wherein the isolated enzyme was used in combination with ADH for the regeneration of NADPH with the use of 2-propanol, as already described. The HPLC analysis showed that UDCA was the only reaction product produced by the enzyme (90% conversion). CDCA (retention time 19.4 min) was not detected in the reaction mixture. The result shows that the enzyme is an NADPH-dependent 7β-HSDH and is capable of the selective reduction of the 7-carbonyl group of 7-keto-LCA to a 7β-hydroxy group.

Retention time UDCA: 15.5 mins

Retention time 7-keto-LCA: 18.3 mins

2. Purification and Gel Filtration

Figure 3:
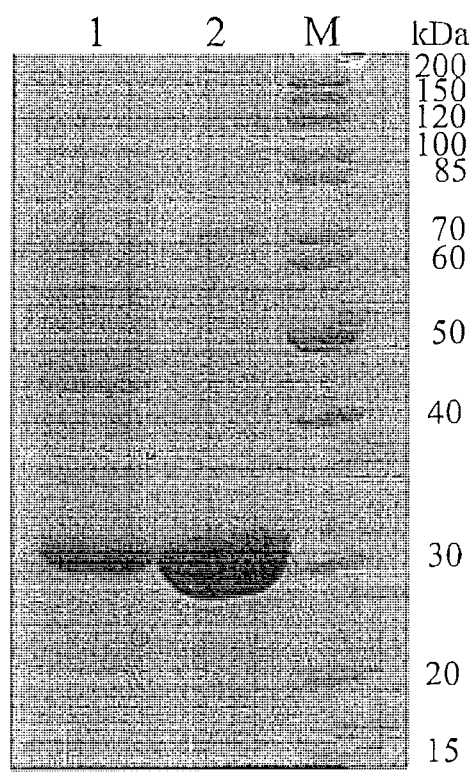
FIG. 3 shows the SDS gel of a purified 7β-HSDH prepared according to the invention, namely on track 1: crude cell extract, track 2: purified protein, and track M: Page Rouler™, molecular weight marker (Fermentas, Germany)

After cloning of the 7β-HSDH gene from *Collinsella aerofaciens* DSM 3979 into the expression vector pET28a (+) and subsequent overexpression, a fusion protein provided with a His-Tag at the N-terminus was obtained with a 7β-HSDH yield of 332.5 mg (5828 U) per liter of culture. The 7/J-HSDH provided with the His-Tag was purified in one step by means of one immobilized metal ions affinity chromatography (purity >90%, yield 76%, see FIG. 3). The main bands of tracks 1 and 2 represent the expected expression product at 30 kDa, which corresponds to the predicted molecular weight derived from the amino acid sequence of the gene. However, by gel filtration a molecular weight of 56.1 kDa is determined for the 7β-HSDH. This confirms the dimeric nature of the 7β-HSDH from *Collinsella aerofaciens* DSM 3979.

3. Sequence Alignments

Figure 4:
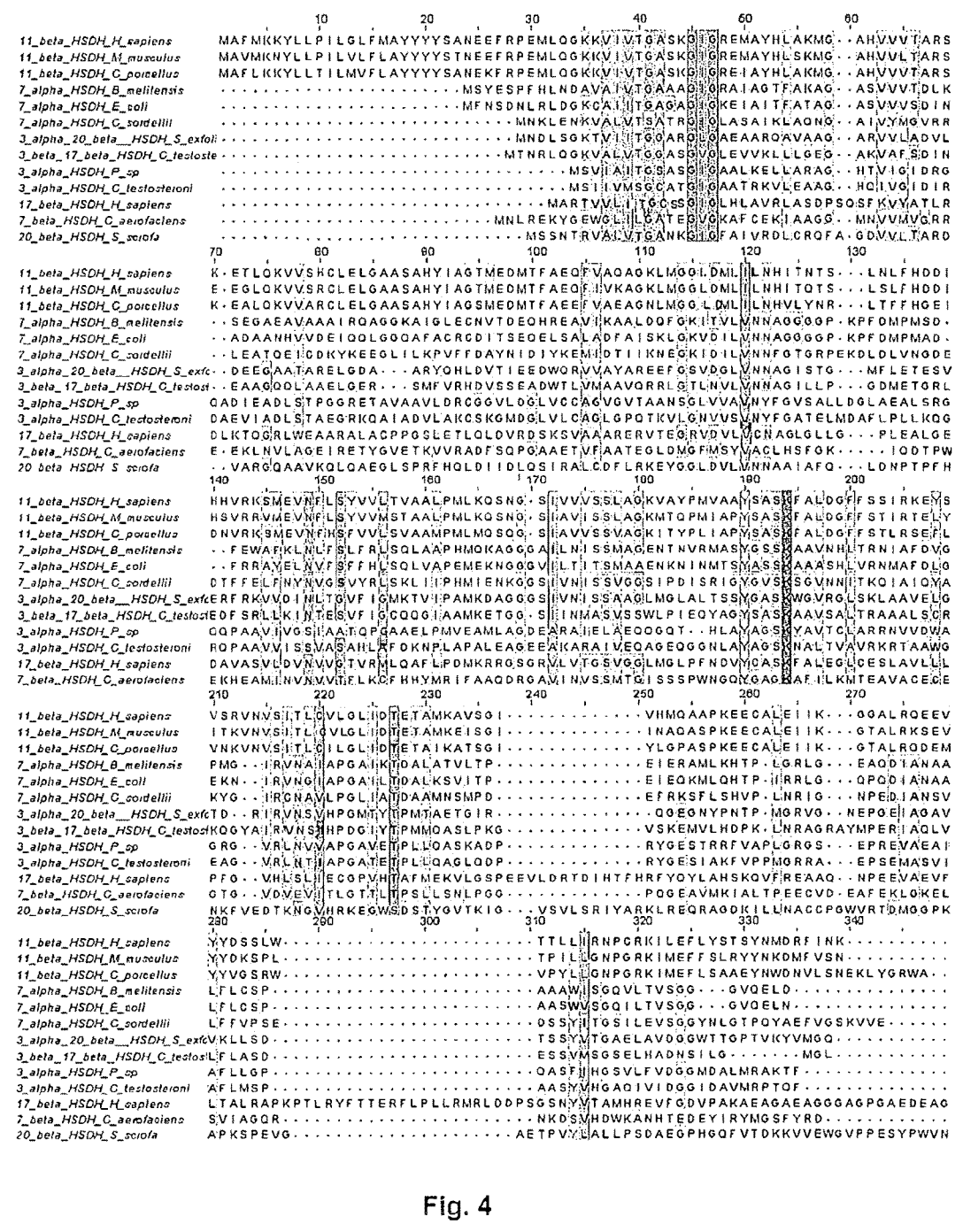

The amino acid sequence of the 7β-HSDH according to the invention was compared with known HSDH sequences (see FIG. 4). The sequence similarity observed indicates that the enzyme according to the invention belongs to the family of the short-chain dehydrogenases (SDR). It is known that SDRs display very low homology and sequence identity (Jornvall, H., B. Persson, M. Krook, S. Atrian, R. Gonzalez-Duarte, J. Jeffery, and D. Ghosh. 1995. Short-chain dehydrogenases/reductases (SDR). Biochemistry 34:6003-13 and Persson, B., M. Krook, and H. Jornvall. 1991. Characteristics of short-chain alcohol dehydrogenases and related enzymes. Eur J Biochem 200:537-43). However, the sequence alignment clearly shows the conserved domains in the SDR primary structure. The N-terminal motif Gly-X-X-X-Gly-X-Gly (corresponding to Gly-41, Gly-45 and Gly-47, numbering corresponding to the alignment) corresponds to the characteristic dinucleotide binding motif of the SDR superfamily. In addition, three strongly conserved residues Ser-177, Tri-190 and Lys-194 (numbering according to alignment) can be discerned, which correspond to the catalytic triads of the SDR enzymes.

4. Phylogenetic Analysis

Figure 5:
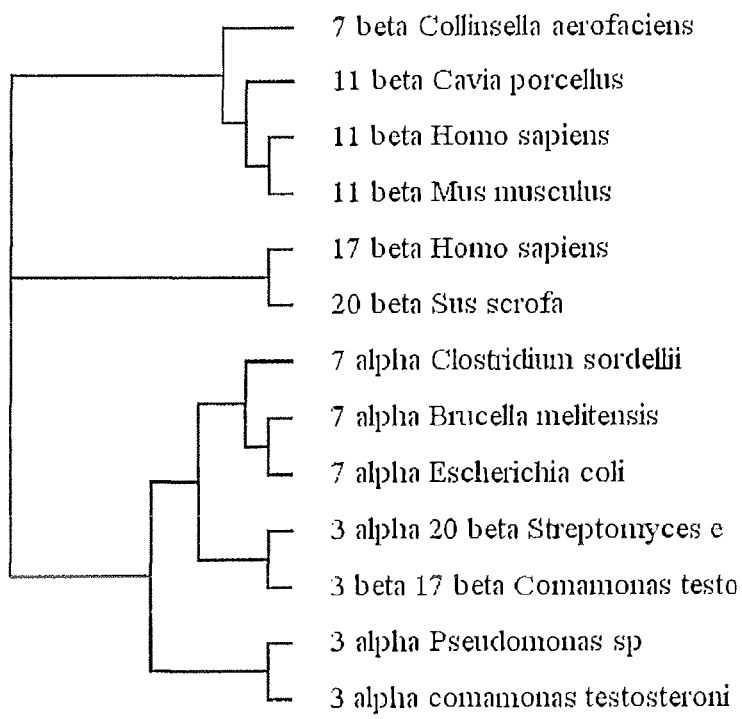
FIG. 5 shows the phylogenetic tree on the basis of an alignment of HSDH protein sequences and illustrates the relatedness between the selected HSDH proteins.

The evolutionary tree based on the alignment of FIG. 4 is shown in FIG. 5. 7β-HSDH from *Clostridium sordellii*, *Brucella melitensis* and *Escherichia coli* belong to the same subgroup. Both 3α-HSDHs shows a more marked relationship than other HSDHs. Interestingly the prokaryotic 7β-HSDH is related to the animal 11β-HSDH subgroup, comprising *Cavia porcellus*, *Homo sapiens* and *Mus musculus*.

5. Kinetic Constants

Kinetic equilibrium analyses were performed in order to determine the absolute values for $V_{MAX}$ and $K_m$ for UDCA, 7-keto-LCA, DHCA, NADP$^+$ and NADPH by means of Lineweaver-Burk plots. In the following table, all kinetic data for the substrates and coenzymes tested, which were obtained from substrate saturation curves and reciprocal plots, are summarized. The $V_{MAX}$, $K_m$ and $k_{cat}$ values for all substrates and coenzymes lie in the same range, whereas the $K_m$ value for DHCA lay significantly higher than with the other substrates, possibly owing to the low solubility in water. The enzyme is NADPH-dependent and kinetic constants for NAD$^+$ and NADH could not be determined owing to the very low activity.

6. pH Optimum

Figure 6:
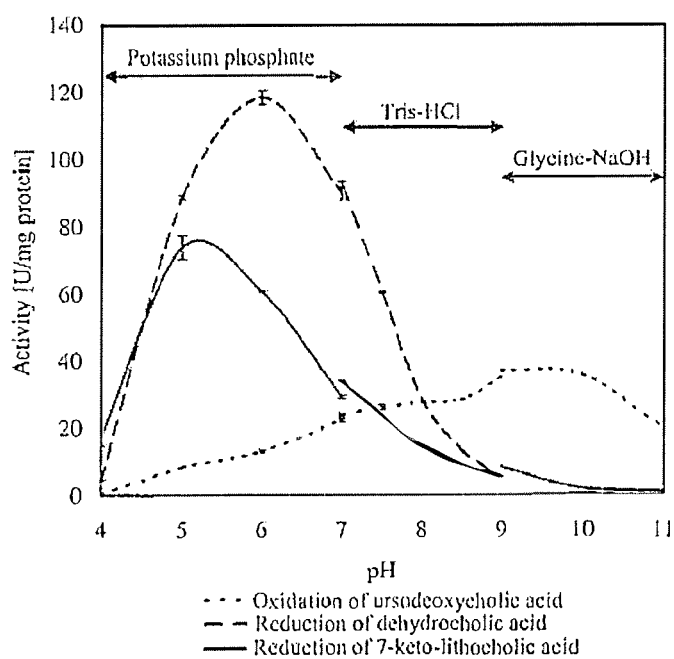
FIG. 6 illustrates the influence of the pH on the activity of the 7β-HSDH according to the invention. The following test conditions were used: pH 4 to 7 in 50 mM potassium phosphate, pH 7 to 9 in 50 mM Tris-HCl and pH 9 to 11 in 50 mM glycine-NaOH at 23° C. The activity values for DHCA and 7-keto-LCA at pH 9 to 11 in 50 mM glycine-NaOH overlap.

Further, the 7β-HSDH activity for various substrates as a function of pH was determined with purified enzyme (see FIG. 6). For the oxidation of UDCA with 7β-HSDH, optimal activity was observed in the range from pH 9 to 10 with a gradual decline on the acidic side. In contrast to this, for the reduction of DHCA and 7-keto-LCA by the 7β-HSDH, optimal activity was found in the range from pH 4 to 6 with a sharp fall on the acidic side and a gradual decline on the alkaline side. Different buffers have only a slight influence on the activity of the 7β-HSDH at the same pH.

7. Thermal Stability

The NADP-dependent 7β-HSDH according to the invention displays the following stability behavior: after 400 mins, the activity at 30° C. was about 30% lower than at 23° C. The enzyme was completely inactivated at 30° C. after 1500 mins, while at 23° C. and 1500 mins the remaining activity was 20%. No significant activity loss was observed during the storage at −20° C. in potassium phosphate buffer (50 mM, pH 8) over a period of a few months after multiple freezing and thawing.

TABLE 1

Summary of kinetic constants for 7β-HSDH from *Collinsella aerofaciens* DSM 3979.

|  | Km (MM) | $V_{max}$ (U/mg protein)[b] | $k_{cat}$ (1 μmol/ (μmol × min)) |
|---|---|---|---|
| NADP$^+$ | 5.32 | 30.58 | 944.95 |
| NADPH | 4.50 | 33.44 | 1033.44 |
| UDCA | 6.23 | 38.17 | 1179.39 |
| 7-keto-LCA | 5.20 | 30.77 | 950.77 |
| DHCA | 9.23 | 28.33 | 875.35 |
| NAD$^+$ | —[a] | — | traces |
| NADH | — | — | traces |

[a] could not be determined owing to the very low activity
[b] 1 U = 1 μmol/min

| SEQ ID No.: | Description | Type |
|---|---|---|
| 1 | 7β-HSDH | NA |
| 2 | 7β-HSDH | AA |
| 3 | Primer | NA |
| 4 | Primer | NA |
| 5 | 3α-HSDH (*C. testosteroni*) | NA |
| 6 | 3α-HSDH (*C. testosteroni*) | AA |
| 7 | 3α-HSDH (*R. norvegicus*) | NA |
| 8 | 3α-HSDH (*R. norvegicus*) | AA |

AA = amino acid sequence
NA = nucleic acid sequence

Reference is explicitly made to the publications mentioned herein.

The invention claimed is:

1. An isolated recombinant 7β-hydroxysteroid dehydrogenase (7β-HSDH) comprising an amino acid sequence according to SEQ ID NO: 2 or an amino acid sequence having only conservative amino acid substitutions as compared to SEQ ID NO: 2 and having at least 95% sequence identity to SEQ ID NO: 2 and a terminal His-Tag sequence, wherein the recombinant 7β-HSDH has a molecular weight, determined by gel filtration, in the range of 53 to 60 kDa, and wherein the recombinant 7β-HSDH is at least capable of catalyzing stereospecific reduction of a 7-ketosteroid to the corresponding 7β-hydroxysteroid.

2. The recombinant 7β-HSDH as claimed in claim 1 that is also capable of catalyzing regiospecific hydrogenation of a ketosteroid in the 7-position to the corresponding 7β-hydroxysteroid.

3. A method for the enzymatic synthesis of 7β-hydroxysteroids, wherein a 7 ketosteroid is reduced in the presence of a recombinant 7β-HSDH as claimed in claim 1, thereby forming the corresponding 7β-hydroxysteroid.

4. The method as claimed in claim 3, wherein the ketosteroid to be reduced is selected from the group consisting of dehydrocholic acid (DHCA), 7-keto-lithocholic acid (7-keto-LCA), 7,12-diketo-lithocholic acid (7,12-diketo-LCA), and salts, amides and alkyl esters thereof.

5. The method as claimed in claim 3, wherein the reduction takes place in the presence of NAD(P)H.

6. A method for the enzymatic oxidation of 7β-hydroxysteroids, wherein the 7β-hydroxysteroid is oxidized in the presence of a 7β-hydroxysteroid dehydrogenase as claimed in claim 1, thereby forming an oxidation product.

7. The method as claimed in claim 6, wherein the M-hydroxysteroid is 3,12-diketo-7β-cholic acid (3,12-diketo-CA) or a salt, amide or alkyl ester thereof.

8. The method as claimed in claim 6, wherein the oxidation takes place in the presence, and with consumption, of NAD(P)+.

9. The method as claimed in claim 5, wherein the redox equivalents consumed are electrochemically or enzymatically regenerated.

10. The method as claimed in claim 9, wherein consumed NAD(P)H is regenerated by coupling with an NAD(P)H-regenerating enzyme selected from the group consisting of an NAD(P)H dehydrogenase and an alcohol dehydrogenase (ADH).

11. The method as claimed in claim 10, wherein the NAD(P)H-regenerating enzyme is selected from the group consisting of isolated and enriched alcohol dehydrogenases classified as (EC 1.1.1.2), wherein said alcohol dehydrogenases are natural or recombinant.

12. A method for the production of ursodesoxycholic acid (UDCA) of the formula (1)

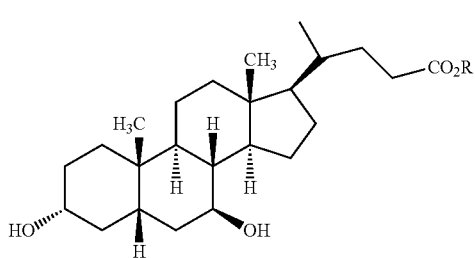

(1)

wherein
R stands for alkyl, $NR^1R^2$, H, an alkali metal ion or $N(R^3)_4^+$, wherein the residues $R^1$, $R^2$ and $R^3$ are the same or different and stand for H or alkyl,
wherein
a) a cholic acid (CA) of the formula (2)

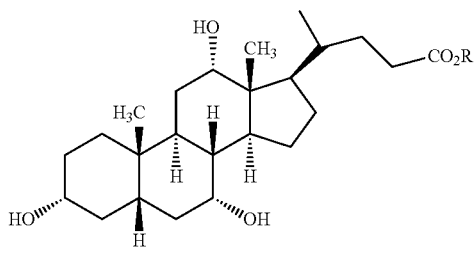

(2)

wherein R has the aforesaid meanings, is optionally chemically oxidized to the dehydrocholic acid (DHCA) of the formula (3)

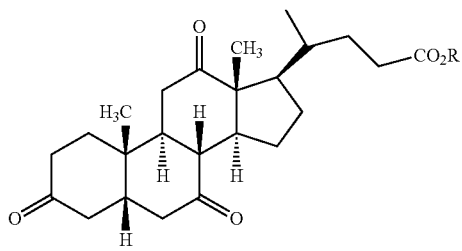

(3)

wherein R has the aforesaid meanings;
b) DHCA is reduced in the presence of a recombinant 7β-HSDH as claimed claim 1 to the 3,12-diketo-7β-cholanic acid (3,12-Diketo-7β-CA) of the formula (4)

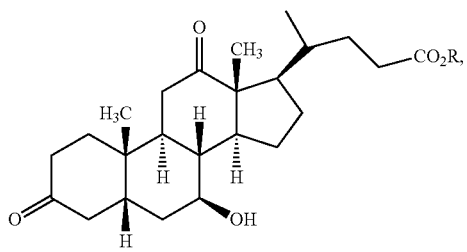

(4)

c) 3,12-diketo-7β-CA is reduced in the presence of at least one 3α-hydroxysteroid dehydrogenase (3α-HSDH) to the corresponding 12-keto-ursodesoxycholic acid (12-keto UDCA) of the formula (5)

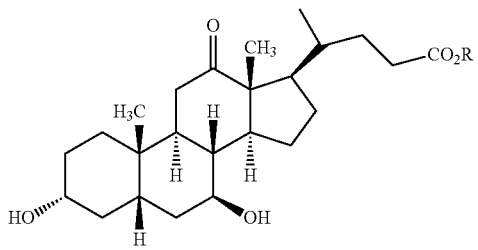

(5)

wherein R has the aforesaid meanings, and then
d) 12-keto-UDCA of the formula (5) is chemically reduced to UDCA; and
e) the reaction product is optionally further purified.

13. The method as claimed in claim 12, wherein the steps b) and/or c) are coupled with a cofactor regeneration step.

14. The method as claimed in claim 12, wherein step b) is coupled with a cofactor regeneration step, in which NADPH is regenerated by alcohol dehydrogenase (ADH) with consumption of a sacrificial alcohol.

15. The method as claimed in claim 12, wherein step c) is coupled with a cofactor regeneration step, in which NADH is regenerated by formate dehydrogenase (FDH) with consumption of formate, or in which NADPH is regenerated by alcohol dehydrogenase (ADH).

16. The recombinant 7β-HSDH as claimed in claim 1, wherein the amino acid sequence has at least 97% sequence identity to SEQ ID NO: 2.

17. An isolated recombinant 7β-hydroxysteroid dehydrogenase (7β-HSDH) comprising an amino acid sequence according to SEQ ID NO: 2 or an amino acid sequence having only conservative amino acid substitutions as compared to SEQ ID NO: 2 and having at least 95% sequence identity to SEQ ID NO: 2 and a terminal His-Tag sequence, wherein the recombinant 7β-HSDH has a molecular weight, determined by gel filtration, in the range of 53 to 60 kDa and is at least capable of catalyzing stereospecific reduction of a 7-ketosteroid to the corresponding 7β-hydroxysteroid, and wherein the recombinant 7β-HSDH is prepared by a process comprising the steps of:
cloning a gene comprising the nucleic acid sequence of SEQ ID NO:1 or a nucleic acid sequence having at least 95% sequence homology with SEQ ID NO:1 and a nucleic acid sequence encoding a His-Tag;
expressing the cloned gene in a bacterial host; and
isolating the expressed protein.

18. The recombinant 7β-HSDH as claimed in claim 17, wherein the gene is cloned in vector pET28a+.

19. The recombinant 7β-HSDH as claimed in claim 17, wherein the bacterial host is *E. coli* BL21(DE3).

20. The recombinant 7β-HSDH as claimed in claim 1 or claim 17, wherein said enzyme comprises a C-terminal or N-terminal His-Tag.

21. The recombinant 7β-HSDH as claimed in claim 20, wherein said enzyme comprises a N-terminal His-Tag.

22. The recombinant 7β-HSDH as claimed in claim 17, comprising an amino acid sequence having at least 97% sequence identity to SEQ ID NO: 2.

* * * * *

SEQUENCE LISTING

```
<160> NUMBER OF SEQ ID NOS: 8

<210> SEQ ID NO 1
<211> LENGTH: 792
<212> TYPE: DNA
<213> ORGANISM: Collinsella aerofaciens
<220> FEATURE:
<221> NAME/KEY: CDS
<222> LOCATION: (1)..(792)

<400> SEQUENCE: 1 atg aac ctg agg gag aag tac ggt gag tgg ggc ctg atc ctg ggc gcg      48
Met Asn Leu Arg Glu Lys Tyr Gly Glu Trp Gly Leu Ile Leu Gly Ala
1               5                  10                  15 acc gag ggc gtc ggc aag gcg ttc tgc gag aag atc gcc gcc ggc ggc      96
Thr Glu Gly Val Gly Lys Ala Phe Cys Glu Lys Ile Ala Ala Gly Gly
            20                  25                  30 atg aac gtc gtc atg gtc ggc cgt cgc gag gag aag ctg aac gtg ctc     144
Met Asn Val Val Met Val Gly Arg Arg Glu Glu Lys Leu Asn Val Leu
        35                  40                  45 gca ggc gag atc cgc gag acc tac ggc gtg gag acc aag gtc gtg cgc     192
Ala Gly Glu Ile Arg Glu Thr Tyr Gly Val Glu Thr Lys Val Val Arg
    50                  55                  60
```

```
gcc gac ttt agc cag ccc ggc gct gcc gag acc gtc ttc gcc gcg acc        240
Ala Asp Phe Ser Gln Pro Gly Ala Ala Glu Thr Val Phe Ala Ala Thr
 65              70                  75                  80 gag ggc ctg gac atg ggc ttc atg agc tac gtg gcc tgc ctg cac agc        288
Glu Gly Leu Asp Met Gly Phe Met Ser Tyr Val Ala Cys Leu His Ser
                 85                  90                  95 ttc ggt aag atc cag gac acc ccc tgg gag aag cac gag gcc atg atc        336
Phe Gly Lys Ile Gln Asp Thr Pro Trp Glu Lys His Glu Ala Met Ile
            100                 105                 110 aac gtc aac gtc gtg acc ttc ctc aag tgc ttc cac cac tac atg cgg        384
Asn Val Asn Val Val Thr Phe Leu Lys Cys Phe His His Tyr Met Arg
        115                 120                 125 atc ttt gcc gcc cag gac cgc ggc gcc gtg atc aac gtc tcg tcg atg        432
Ile Phe Ala Ala Gln Asp Arg Gly Ala Val Ile Asn Val Ser Ser Met
    130                 135                 140 acc ggc atc agc tcc agc ccc tgg aac ggc cag tac ggc gcg ggc aag        480
Thr Gly Ile Ser Ser Ser Pro Trp Asn Gly Gln Tyr Gly Ala Gly Lys
145                 150                 155                 160 gcc ttc atc ctc aag atg acc gag gcc gtg gcc tgc gag tgc gag ggc        528
Ala Phe Ile Leu Lys Met Thr Glu Ala Val Ala Cys Glu Cys Glu Gly
                165                 170                 175 acc ggc gtc gac gtc gag gtc atc acc ctc ggc acc acc cta acc ccc        576
Thr Gly Val Asp Val Glu Val Ile Thr Leu Gly Thr Thr Leu Thr Pro
            180                 185                 190 agc ctg ctg tcc aac ctc ccc ggc ggc ccg cag ggc gag gcc gtc atg        624
Ser Leu Leu Ser Asn Leu Pro Gly Gly Pro Gln Gly Glu Ala Val Met
        195                 200                 205 aag atc gcc ctc acc ccc gag gag tgc gtt gac gag gcc ttt gag aag        672
Lys Ile Ala Leu Thr Pro Glu Glu Cys Val Asp Glu Ala Phe Glu Lys
    210                 215                 220 ctg ggt aag gag ctc tcc gtc atc gcc ggc cag cgc aac aag gac tcc        720
Leu Gly Lys Glu Leu Ser Val Ile Ala Gly Gln Arg Asn Lys Asp Ser
225                 230                 235                 240 gtc cac gac tgg aag gca aac cac acc gag gac gag tac atc cgc tac        768
Val His Asp Trp Lys Ala Asn His Thr Glu Asp Glu Tyr Ile Arg Tyr
                245                 250                 255 atg ggg tcg ttc tac cgc gac tag                                        792
Met Gly Ser Phe Tyr Arg Asp
            260

<210> SEQ ID NO 2
<211> LENGTH: 263
<212> TYPE: PRT
<213> ORGANISM: Collinsella aerofaciens

<400> SEQUENCE: 2

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
                20                  25                  30

Met Asn Val Val Met Val Gly Arg Arg Glu Glu Lys Leu Asn Val Leu
            35                  40                  45

Ala Gly Glu Ile Arg Glu Thr Tyr Gly Val Gly Thr Lys Val Val Arg
        50                  55                  60

Ala Asp Phe Ser Gln Pro Gly Ala Ala Glu Thr Val Phe Ala Ala Thr
65              70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
```

```
                100              105               110
Asn Val Asn Val Val Thr Phe Leu Lys Cys Phe His His Tyr Met Arg
                115                  120                 125
Ile Phe Ala Ala Gln Asp Arg Gly Ala Val Ile Asn Val Ser Ser Met
                130                 135                 140
Thr Gly Ile Ser Ser Ser Pro Trp Asn Gly Gln Tyr Gly Ala Gly Lys
145                 150                 155                 160
Ala Phe Ile Leu Lys Met Thr Glu Ala Val Ala Cys Glu Cys Glu Gly
                165                 170                 175
Thr Gly Val Asp Val Glu Val Ile Thr Leu Gly Thr Thr Leu Thr Pro
                180                 185                 190
Ser Leu Leu Ser Asn Leu Pro Gly Gly Pro Gln Gly Glu Ala Val Met
                195                 200                 205
Lys Ile Ala Leu Thr Pro Glu Glu Cys Val Asp Glu Ala Phe Glu Lys
                210                 215                 220
Leu Gly Lys Glu Leu Ser Val Ile Ala Gly Gln Arg Asn Lys Asp Ser
225                 230                 235                 240
Val His Asp Trp Lys Ala Asn His Thr Glu Asp Glu Tyr Ile Arg Tyr
                245                 250                 255
Met Gly Ser Phe Tyr Arg Asp
            260
```

```
<210> SEQ ID NO 3
<211> LENGTH: 31
<212> TYPE: DNA
<213> ORGANISM: artificial
<220> FEATURE:
<223> OTHER INFORMATION: PCR Primer

<400> SEQUENCE: 3
gggaattcca tatgaacctg agggagaagt a                               31

<210> SEQ ID NO 4
<211> LENGTH: 27
<212> TYPE: DNA
<213> ORGANISM: Artificial
<220> FEATURE:
<223> OTHER INFORMATION: PCR Primer

<400> SEQUENCE: 4
cccaagcttc tagtcgcggt agaacga                                    27

<210> SEQ ID NO 5
<211> LENGTH: 774
<212> TYPE: DNA
<213> ORGANISM: Comamonas testosteroni
<220> FEATURE:
<221> NAME/KEY: CDS
<222> LOCATION: (1)..(774)

<400> SEQUENCE: 5
```

```
atg tcc atc atc gtg ata agc ggc tgc gcc acc ggc att ggt gcg gct    48
Met Ser Ile Ile Val Ile Ser Gly Cys Ala Thr Gly Ile Gly Ala Ala
1               5                   10                  15 acg cgc aag gtc ctg gag gcg gcc ggt cac cag atc gta ggc atc gat    96
Thr Arg Lys Val Leu Glu Ala Ala Gly His Gln Ile Val Gly Ile Asp
                20                  25                  30 ata cgc gat gcg gaa gtg att gcc gat ctc tcg acg gcc gaa ggt cga   144
Ile Arg Asp Ala Glu Val Ile Ala Asp Leu Ser Thr Ala Glu Gly Arg
            35                  40                  45
```

-continued

| | | |
|---|---|---|
| aag cag gcg att gcc gat gta ctg gcg aag tgc agc aag ggc atg gac<br>Lys Gln Ala Ile Ala Asp Val Leu Ala Lys Cys Ser Lys Gly Met Asp<br>50                       55                   60 | | 192 |
| ggc ctg gtg ctg tgc gcc ggc ctg gga ccg cag acc aag gtg ctt ggc<br>Gly Leu Val Leu Cys Ala Gly Leu Gly Pro Gln Thr Lys Val Leu Gly<br>65                       70                   75                   80 | | 240 |
| aat gtg gtt tcg gtc aat tat ttt ggc gcg acc gag ctg atg gat gcc<br>Asn Val Val Ser Val Asn Tyr Phe Gly Ala Thr Glu Leu Met Asp Ala<br>                      85                   90                   95 | | 288 |
| ttt ttg cca gcg ctg aaa aaa ggc cat cag ccc gca gcc gtc gtc atc<br>Phe Leu Pro Ala Leu Lys Lys Gly His Gln Pro Ala Ala Val Val Ile<br>                    100                  105                 110 | | 336 |
| tcg tcc gtg gct tcc gcg cat ctg gct ttt gac aag aac cca ctg gcg<br>Ser Ser Val Ala Ser Ala His Leu Ala Phe Asp Lys Asn Pro Leu Ala<br>                 115                  120                 125 | | 384 |
| ctg gca ctg gaa gcc ggc gag gaa gcc aag gcc cgc gcc att gtc gaa<br>Leu Ala Leu Glu Ala Gly Glu Glu Ala Lys Ala Arg Ala Ile Val Glu<br>130                       135                   140 | | 432 |
| cat gcg gga gag cag ggc gga aat ctg gcc tat gcg ggc agc aag aat<br>His Ala Gly Glu Gln Gly Gly Asn Leu Ala Tyr Ala Gly Ser Lys Asn<br>145                       150                   155                 160 | | 480 |
| gct ttg acg gtg gct gtg cgc aaa cgc gcc gcc gcc tgg ggc gag gct<br>Ala Leu Thr Val Ala Val Arg Lys Arg Ala Ala Ala Trp Gly Glu Ala<br>                 165                  170                 175 | | 528 |
| ggc gtg cgc ctg aac acc atc gcc ccc ggt gca acc gag act ccc ttg<br>Gly Val Arg Leu Asn Thr Ile Ala Pro Gly Ala Thr Glu Thr Pro Leu<br>                     180                  185                 190 | | 576 |
| ctg cag gcg ggc ctg cag gac ccg cgc tat ggc gaa tcc att gcc aag<br>Leu Gln Ala Gly Leu Gln Asp Pro Arg Tyr Gly Glu Ser Ile Ala Lys<br>               195                  200                 205 | | 624 |
| ttc gtt cct ccc atg ggc cgc cgt gcc gag ccg tcc gag atg gcg tcg<br>Phe Val Pro Pro Met Gly Arg Arg Ala Glu Pro Ser Glu Met Ala Ser<br>210                       215                   220 | | 672 |
| gtc atc gcc ttt ttg atg agc ccg gcc gca agc tat gtg cat ggc gcg<br>Val Ile Ala Phe Leu Met Ser Pro Ala Ala Ser Tyr Val His Gly Ala<br>225                       230                   235                 240 | | 720 |
| cag atc gtc att gat ggc ggc att gat gcg gtg atg cgc ccg aca cag<br>Gln Ile Val Ile Asp Gly Gly Ile Asp Ala Val Met Arg Pro Thr Gln<br>                     245                  250                 255 | | 768 |
| ttc tga<br>Phe | | 774 |

<210> SEQ ID NO 6
<211> LENGTH: 257
<212> TYPE: PRT
<213> ORGANISM: Comamonas testosteroni

<400> SEQUENCE: 6

Met Ser Ile Ile Val Ile Ser Gly Cys Ala Thr Gly Ile Gly Ala Ala
1                   5                   10                 15

Thr Arg Lys Val Leu Glu Ala Ala Gly His Gln Ile Val Gly Ile Asp
                  20                  25                  30

Ile Arg Asp Ala Glu Val Ile Ala Asp Leu Ser Thr Ala Glu Gly Arg
             35                  40                  45

Lys Gln Ala Ile Ala Asp Val Leu Ala Lys Cys Ser Lys Gly Met Asp
       50                  55                  60

Gly Leu Val Leu Cys Ala Gly Leu Gly Pro Gln Thr Lys Val Leu Gly
65                   70                   75                   80

Asn Val Val Ser Val Asn Tyr Phe Gly Ala Thr Glu Leu Met Asp Ala

```
                85                  90                  95
Phe Leu Pro Ala Leu Lys Lys Gly His Gln Pro Ala Ala Val Val Ile
            100                 105                 110

Ser Ser Val Ala Ser Ala His Leu Ala Phe Asp Lys Asn Pro Leu Ala
            115                 120                 125

Leu Ala Leu Glu Ala Gly Glu Glu Ala Lys Ala Arg Ala Ile Val Glu
        130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Ala Trp Gly Glu Ala
                165                 170                 175

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe
```

<210> SEQ ID NO 7
<211> LENGTH: 969
<212> TYPE: DNA
<213> ORGANISM: Rattus norvegicus
<220> FEATURE:
<221> NAME/KEY: CDS
<222> LOCATION: (1)..(969)

<400> SEQUENCE: 7

```
atg gat tcc ata tct ctg cgt gta gca cta aat gat ggt aac ttc att    48
Met Asp Ser Ile Ser Leu Arg Val Ala Leu Asn Asp Gly Asn Phe Ile
1               5                   10                  15 cct gta ctg ggg ttt gga acc act gtg cct gag aag gtt gct aag gat    96
Pro Val Leu Gly Phe Gly Thr Thr Val Pro Glu Lys Val Ala Lys Asp
            20                  25                  30 gaa gtt atc aag gct act aaa ata gct ata gat aat gga ttc cgc cat   144
Glu Val Ile Lys Ala Thr Lys Ile Ala Ile Asp Asn Gly Phe Arg His
        35                  40                  45 ttt gac tct gct tat ttg tac gaa gta gaa gag gaa gtg ggc caa gcc   192
Phe Asp Ser Ala Tyr Leu Tyr Glu Val Glu Glu Glu Val Gly Gln Ala
    50                  55                  60 att aga agc aag att gaa gac ggc act gtg aag aga gaa gat ata ttc   240
Ile Arg Ser Lys Ile Glu Asp Gly Thr Val Lys Arg Glu Asp Ile Phe
65                  70                  75                  80 tat act tca aag ctt tgg agc act ttc cat aga cca gag ctg gtc cga   288
Tyr Thr Ser Lys Leu Trp Ser Thr Phe His Arg Pro Glu Leu Val Arg
                85                  90                  95 act tgc ttg gaa aag aca ctg aaa agc act caa ctg gac tat gtg gat   336
Thr Cys Leu Glu Lys Thr Leu Lys Ser Thr Gln Leu Asp Tyr Val Asp
            100                 105                 110 ctt tat att att cat ttc cca atg gct ttg cag cct gga gat ata ttt   384
Leu Tyr Ile Ile His Phe Pro Met Ala Leu Gln Pro Gly Asp Ile Phe
        115                 120                 125 ttc cca cga gat gag cat gga aaa cta ttg ttt gaa aca gtg gat atc   432
Phe Pro Arg Asp Glu His Gly Lys Leu Leu Phe Glu Thr Val Asp Ile
```

```
            130                 135                 140
tgt aca tgg gag gcc atg gaa aag tgt aag gat gca gga ttg gcc       480
Cys Asp Thr Trp Glu Ala Met Glu Lys Cys Lys Asp Ala Gly Leu Ala
145                 150                 155                 160 aag tct att ggg gtg tcc aac ttt aac tgc agg cag ctg gag agg att   528
Lys Ser Ile Gly Val Ser Asn Phe Asn Cys Arg Gln Leu Glu Arg Ile
                165                 170                 175 ctg aat aag cca ggg ctc aaa tac aag cct gtg tgc aac cag gtg gaa   576
Leu Asn Lys Pro Gly Leu Lys Tyr Lys Pro Val Cys Asn Gln Val Glu
        180                 185                 190 tgt cac ctt tat ctc aac cag agc aaa atg ctg gac tat tgt aag tca   624
Cys His Leu Tyr Leu Asn Gln Ser Lys Met Leu Asp Tyr Cys Lys Ser
    195                 200                 205 aaa gac atc att ctg gtt tcc tac tgc acg ctg gga agt tca cga gac   672
Lys Asp Ile Ile Leu Val Ser Tyr Cys Thr Leu Gly Ser Ser Arg Asp
210                 215                 220 aaa aca tgg gtg gat cag aaa agt cca gtt ctc cta gat gat cca gtt   720
Lys Thr Trp Val Asp Gln Lys Ser Pro Val Leu Leu Asp Asp Pro Val
225                 230                 235                 240 ctt tgt gcc ata gca aag aag tac aag caa acc cca gcc cta gtt gcc   768
Leu Cys Ala Ile Ala Lys Lys Tyr Lys Gln Thr Pro Ala Leu Val Ala
                245                 250                 255 ctt cgc tac cag ctg cag cgt ggg gtt gtg ccc ctg atc agg agt ttc   816
Leu Arg Tyr Gln Leu Gln Arg Gly Val Val Pro Leu Ile Arg Ser Phe
        260                 265                 270 aac gcg aag cgg atc aaa gag cta aca cag gtt ttt gaa ttc cag ttg   864
Asn Ala Lys Arg Ile Lys Glu Leu Thr Gln Val Phe Glu Phe Gln Leu
    275                 280                 285 gct tca gag gac atg aaa gcc ctg gat ggc ttg aac aga aat ttc aga   912
Ala Ser Glu Asp Met Lys Ala Leu Asp Gly Leu Asn Arg Asn Phe Arg
290                 295                 300 tac aac aat gca aaa tat ttt gat gac cat ccc aat cat cca ttt act   960
Tyr Asn Asn Ala Lys Tyr Phe Asp Asp His Pro Asn His Pro Phe Thr
305                 310                 315                 320 gat gaa tag                                                       969
Asp Glu

<210> SEQ ID NO 8
<211> LENGTH: 322
<212> TYPE: PRT
<213> ORGANISM: Rattus norvegicus

<400> SEQUENCE: 8

Met Asp Ser Ile Ser Leu Arg Val Ala Leu Asn Asp Gly Asn Phe Ile
1               5                   10                  15

Pro Val Leu Gly Phe Gly Thr Thr Val Pro Glu Lys Val Ala Lys Asp
            20                  25                  30

Glu Val Ile Lys Ala Thr Lys Ile Ala Ile Asp Asn Gly Phe Arg His
        35                  40                  45

Phe Asp Ser Ala Tyr Leu Tyr Glu Val Glu Glu Val Gly Gln Ala
    50                  55                  60

Ile Arg Ser Lys Ile Glu Asp Gly Thr Val Lys Arg Glu Asp Ile Phe
65                  70                  75                  80

Tyr Thr Ser Lys Leu Trp Ser Thr Phe His Arg Pro Glu Leu Val Arg
                85                  90                  95

Thr Cys Leu Glu Lys Thr Leu Lys Ser Thr Gln Leu Asp Tyr Val Asp
            100                 105                 110

Leu Tyr Ile Ile His Phe Pro Met Ala Leu Gln Pro Gly Asp Ile Phe
```

```
                    115                 120                 125
Phe Pro Arg Asp Glu His Gly Lys Leu Leu Phe Glu Thr Val Asp Ile
        130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Cys Arg Gln Leu Glu Arg Ile
                165                 170                 175

Leu Asn Lys Pro Gly Leu Lys Tyr Lys Pro Val Cys Asn Gln Val Glu
            180                 185                 190

Cys His Leu Tyr Leu Asn Gln Ser Lys Met Leu Asp Tyr Cys Lys Ser
        195                 200                 205

Lys Asp Ile Ile Leu Val Ser Tyr Cys Thr Leu Gly Ser Ser Arg Asp
    210                 215                 220

Lys Thr Trp Val Asp Gln Lys Ser Pro Val Leu Leu Asp Asp Pro Val
225                 230                 235                 240

Leu Cys Ala Ile Ala Lys Lys Tyr Lys Gln Thr Pro Ala Leu Val Ala
                245                 250                 255

Leu Arg Tyr Gln Leu Gln Arg Gly Val Val Pro Leu Ile Arg Ser Phe
            260                 265                 270

Asn Ala Lys Arg Ile Lys Glu Leu Thr Gln Val Phe Glu Phe Gln Leu
        275                 280                 285

Ala Ser Glu Asp Met Lys Ala Leu Asp Gly Leu Asn Arg Asn Phe Arg
    290                 295                 300

Tyr Asn Asn Ala Lys Tyr Phe Asp Asp His Pro Asn His Pro Phe Thr
305                 310                 315                 320

Asp Glu
```